United States Patent [19]
Okada

[11] Patent Number: 5,706,542
[45] Date of Patent: Jan. 13, 1998

[54] ELECTRICALLY DRIVEN TOOTHBRUSH

[76] Inventor: Eiji Okada, 5-15-5 Nakanobu, Shinagawa-ku, Tokyo, Japan

[21] Appl. No.: 655,979

[22] Filed: May 31, 1996

[30] Foreign Application Priority Data

Jun. 27, 1995 [JP] Japan ............................ 7-183371
Dec. 19, 1995 [JP] Japan ............................ 7-348741

[51] Int. Cl.$^6$ ............................ A61C 17/00; A46B 13/02
[52] U.S. Cl. ............................................................ 15/22.1
[58] Field of Search ............................ 15/22.1, 22.3, 15/21.2, 23, 28; 200/502, 542, 544, 537, 560, 573

[56] References Cited

U.S. PATENT DOCUMENTS

| 3,029,451 | 4/1962 | Barr | 15/23 |
|---|---|---|---|
| 3,104,405 | 9/1963 | Parrinjaquet | 15/22.1 |
| 3,183,538 | 5/1965 | Hubner | |
| 3,196,299 | 7/1965 | Kott | 15/22.1 |
| 3,300,664 | 1/1967 | Boyles | 15/22.1 |
| 3,466,689 | 9/1969 | Aurelio et al. | |
| 3,535,726 | 10/1970 | Sawyer | |
| 3,685,080 | 8/1972 | Hubner | |
| 4,374,354 | 2/1983 | Petrovic et al. | |
| 5,383,242 | 1/1995 | Bigler et al. | |
| 5,421,726 | 6/1995 | Okada | |
| 5,524,312 | 6/1996 | Tan et al. | 15/22.1 |

FOREIGN PATENT DOCUMENTS

| 2659348 | 9/1991 | France | 15/23 |
|---|---|---|---|
| 3937878 | 4/1991 | Germany | 15/22.1 |
| 40-12541 | 6/1940 | Japan . | |
| 53-21650 | 2/1978 | Japan . | |
| 61-217109 | 9/1986 | Japan . | |
| 5-4918 | 1/1993 | Japan . | |
| 5-11829 | 2/1993 | Japan . | |
| 133819 | 5/1994 | Japan | 15/22.1 |
| 2116027 | 9/1983 | United Kingdom | 15/23 |

*Primary Examiner*—Tony G. Soohoo
*Attorney, Agent, or Firm*—Flynn, Thiel, Boutell & Tanis, P.C.

[57] ABSTRACT

An electrically driven toothbrush that includes a switch lever engaged with a hole for switching a motor on and off, the hole being defined through an end wall of a dry cell cap. The switch lever includes a manipulation control portion, a revolving shaft portion, a spherical operating portion, and a lever portion, all formed integrally by a flexible member. The toothbrush includes an electric circuit-connecting terminal structure for joining the motor and dry cell in communication with one another, which terminal structure is formed by first and second terminal members. The first and second terminal members each includes a platelike L-shaped main body, and the platelike main body of the second terminal member is resilient so as to return to a predetermined L-shape when no external forces are exerted thereon.

10 Claims, 26 Drawing Sheets

FIG. 27
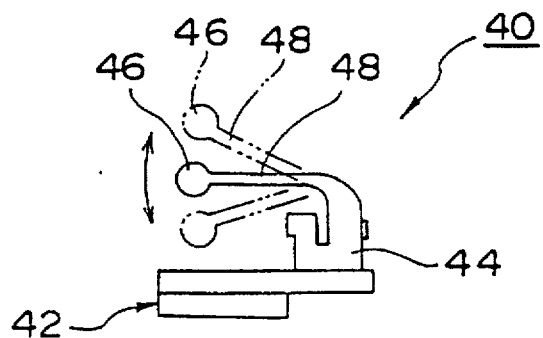
FIG. 28A        FIG. 28B        FIG. 28C
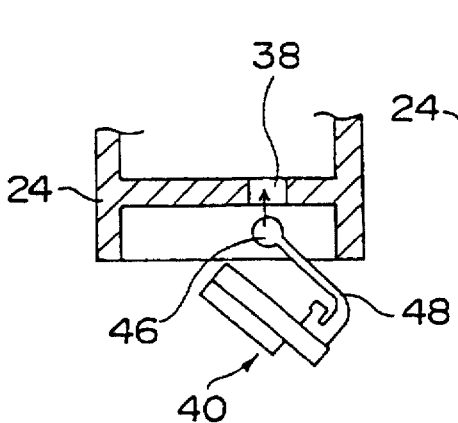  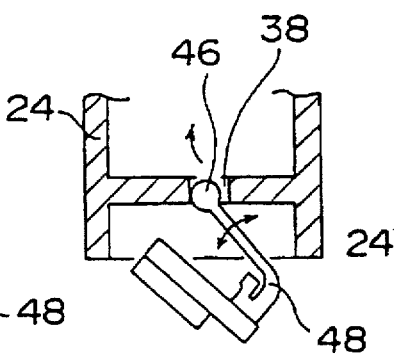  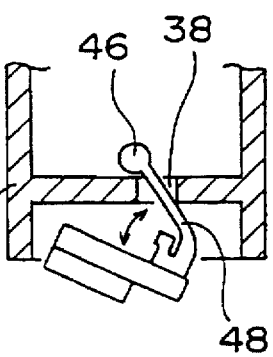
FIG. 28D        FIG. 28E
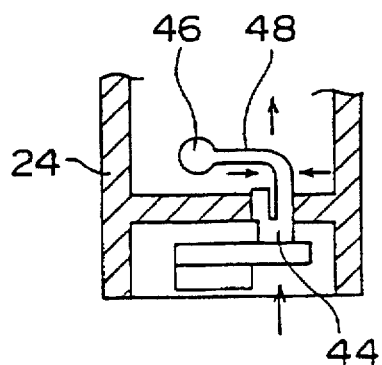  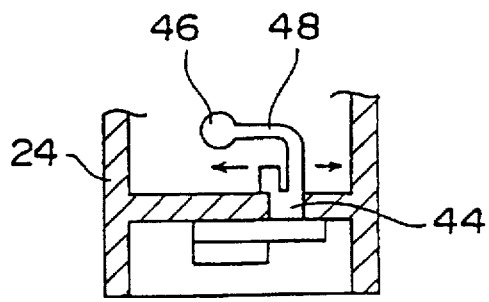

FIG. 74
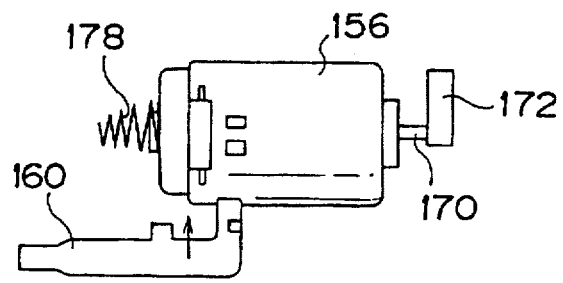
FIG. 75
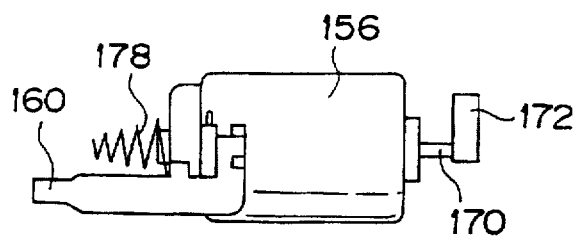
FIG. 76
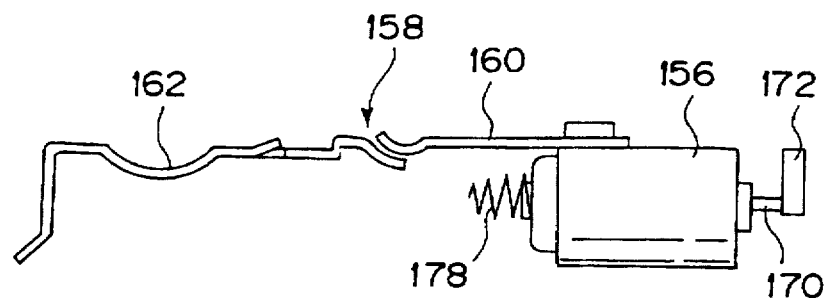
FIG. 77A    FIG. 77B
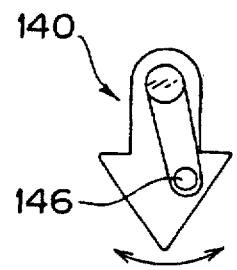
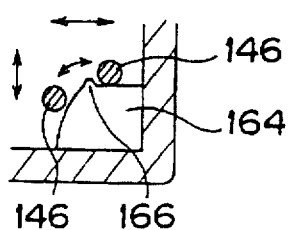

ELECTRICALLY DRIVEN TOOTHBRUSH

FIELD OF THE INVENTION

This invention relates to an electrically driven toothbrush, and more particularly, to an electrically driven toothbrush that includes simpler structured components for cost saving.

This invention also relates to an electrically driven toothbrush which is designed for sufficiently tight assembly to prevent the occurrence of loosening in the assembled toothbrush, and which is constructed to positively retain a dry cell therein.

BACKGROUND OF THE INVENTION

Among toothbrushes, there is a general type of toothbrush designed for manual use, in which a handle portion is formed integrally with a toothbrushing portion. Apart from the foregoing, a power-driven toothbrush, which houses an electrically operated motor, is available. The motor is actuated by electric current from a dry cell or alternatively a receptacle.

There are several methods for cleaning the teeth using an electrically driven toothbrush, and some of them are as follows: the Bass method for moving a brushing portion of the toothbrush in a short and quick motion in a state where the bristles on the toothbrushing portion are held in contact with the gums as well as the teeth at about a 45 degree angle; the rolling method for pivoting a handle portion of the toothbrush with a flick of the wrist about the axis of the handle portion, thereby pivoting the toothbrushing portion; the Fones method for moving the bristles in a circular motion in contact with the teeth at a right angle; and, the scrapping method for moving the bristles in a short and quick motion in a state where the bristle tips are being positioned in contact with the teeth at a right angle.

The tooth-cleaning method may be classified broadly into the above four different types, although it varies from user to user depending on individual difference such as rows of the teeth, user's habits of brushing the teeth, and types or extent of periodontal ailments.

Further, there are some schools in which the dental profession provides guidance to pupils about toothbrushing as a part of educational programs. This system teaches them appropriate methods for cleaning the teeth so as to provide dental health care or healing in light of the state or condition of the teeth.

The electrically driven toothbrush has been developed for the purpose of achieving a reduction in time for brushing the teeth and an improvement in convenience of use, as compared with manually operated toothbrushes.

Such a power-driven toothbrush may be classed as a conversion type of toothbrush and a vibration type of toothbrush. The former toothbrush has an electrically operated motor disposed therein for producing a revolving force, and further has a revolving force-converting mechanism disposed therein for changing the revolving force into, e.g., a rolling motion or otherwise a sliding motion. The vibration type of toothbrush has an eccentric weight attached to the electrically operated motor. Either type of the above toothbrushes is a hygienic appliance whose toothbrushing portion is positioned in contact with the teeth so as to brush tooth surfaces and massage the gums as well, thereby protecting the teeth and the gums against ailments.

The electrically driven toothbrush is typically constructed to allow the toothbrushing portion to be removed from the handle portion in order that the toothbrushing portion is replaceable when the degraded function of the bristles, such as deformation etc., occurs over long periods of use.

As a way of manually opening and closing an electric circuit in the toothbrush, there are mechanical types of switching mechanisms, such as a toggle switch, a slide switch, a push switch, a seesaw switch, a rotary switch, and the like.

In conventional power-driven toothbrushes, mounting portions having complicated structures are used when the toothbrush is assembled, i.e., when the toothbrushing portion or the motor is mounted to or into the handle portion, or when a dry cell cap is attached to the handle portion. In addition, the mount portions become loose after the assembly of the toothbrush. Furthermore, a dry cell cannot always be positively retained within the toothbrush.

This results in an inconvenience in that the electrically driven toothbrush, and in particular, the aforesaid mounting portions, are costly and difficult to manufacture, which is disadvantageous from an economical viewpoint.

There is another inconvenience in that the complicated structure of the mounting components may greatly increase the dimension and weight of the power-driven toothbrush, and such a toothbrush is inconvenient for use.

Yet another inconvenience arises when the power-driven toothbrush is used in combination with any switch of a conventional finished article. More specifically, such a switch is of predetermined and limited configuration and size; and, the toothbrush, in which the aforesaid switch is to be incorporated, is subjected to certain restrictions so as to provide its original design. As a result, inconsistence or otherwise enforced matching occurs in respect of dimensions, mechanical systems, or switch design.

Further inconvenience is that the electrically driven toothbrush is inconvenient for use because the handle portion, the motor, the dry cell cap, and the like become loose after the toothbrush is assembled.

Yet further inconvenience is that, since the dry cell cannot be positively retained when being placed within the dry cell cap, the dry cell emits a rattling noise as a result of the toothbrush being in vibration during the use of the toothbrush, which is disadvantageous in view of practical use.

In order to eliminate the above-described inconveniences, one aspect of the present invention provides an electrically driven toothbrush including a handle portion, an electrically operated motor accommodated in the handle portion, a toothbrushing portion engaged with one end of the handle portion, a dry cell cap having a dry cell (i.e. a battery) disposed therein so as to be engaged with the other end of the handle portion, and an eccentric weight for producing vibration when the motor is actuated, thereby bringing the toothbrushing portion into vibration which is utilized to clean the teeth, the improvement comprising: a switch lever engaged with a hole portion for switching the motor on and off, the hole portion being defined through an end surface of the dry cell cap, wherein the switch lever includes a manipulation control portion positioned outside the dry cell cap when the switch lever is engaged with the dry cell cap, a revolving shaft portion fixedly attached to the manipulation control portion and sealingly fitted in the hole portion, a spherical operating portion positioned inside the dry cell cap, and a lever portion having the spherical operating portion and the revolving shaft portion in communication with one another, and wherein these components of the switch lever are formed integrally by a flexible member.

Another aspect of the present invention provides an electrically driven toothbrush including a handle portion, an electrically operated motor accommodated in the handle portion, a toothbrushing portion engaged with one end of the handle portion, a dry cell cap having a dry cell disposed therein so as to be engaged with the other end of the handle portion, and an eccentric weight for producing vibration when the motor is actuated, thereby bringing the toothbrushing portion into vibration which is utilized to clean the teeth, the improvement comprising: a switch lever engaged with a hole portion for switching the motor on and off, the hole portion being defined through an end surface of the dry cell cap; and, an electric circuit-connecting terminal for connecting the motor and the dry cell in communication with one another in order to actuate the motor, the electric circuit-connecting terminal being formed by a first terminal whose one end contacts the motor, while the other end of the first terminal extends toward the dry cell, and further by a second terminal whose one end contacts the other end of the first terminal, while the other end of the second terminal communicates with the switch lever, extending over the dry cell, wherein the first terminal includes a platelike main body of an electrically conductive metallic member formed into a L-shaped configuration, a first cut and raised portion formed on part of a shorter side of the platelike main body, a second cut and raised portion formed on a longer side of the platelike main body and adjacent to a location where the longer and shorter sides of the platelike main body communicate with one another, a bent portion formed adjacent to the second cut and raised portion, and a curved portion formed at an end portion of the longer side of the platelike main body, wherein the second terminal includes a platelike main body of an electrically conductive metallic member bent into a L-shape in cross-section, a contact portion formed at one end portion of the platelike main body for contacting the curved portion of the first terminal, a cut and raised portion formed substantially midway along the platelike main body, a bent portion formed by the other end portion of the platelike main body being slightly decreased in width dimension and further being bent into a L-shape in cross-section, and a swinging end portion bent and formed at an end portion of the bent portion so as to be directed downward, and wherein the platelike main body of the second terminal has resilient force imparted thereto so as to spring back to a predetermined L-shape in cross-section when no external forces are exerted on the platelike main body of the second terminal.

Still another aspect of the invention is a toothbrush, as aforesaid, wherein the platelike main body of the second terminal has a dry cell-pressing portion provided between the cut and raised portion and the bent portion, the dry cell-pressing portion being arcuate in shape, and protruding toward the dry cell so as to press and retain the dry cell when the dry cell is placed into the dry cell cap.

A further aspect of the present invention provides an electrically driven toothbrush including a handle portion, an electrically operated motor accommodated in the handle portion, a toothbrushing portion engaged with one end of the handle portion, a dry cell cap housing a dry cell so as to be engaged with the other end of the handle portion, and an eccentric weight for producing vibration when the motor is actuated, thereby bringing the toothbrushing portion into vibration that is utilized to clean the teeth, the improvement comprising: band-shaped, first engagement protrusions extending in a transverse direction of the handle portion, the first engagement protrusions being provided on opposing inner peripheral surface portions of the handle portion; and, band-shaped, second engagement protrusions extending in a transverse direction of the dry cell cap, the second engagement protrusions being provided on outer peripheral surface portions at opposing side portions of the dry cell cap so as to be engaged with the first engagement protrusions.

Pursuant to a still further aspect of the present invention, there is provided an electrically driven toothbrush including a handle portion, an electrically operated motor accommodated in the handle portion, a toothbrushing portion engaged with one end of the handle portion, a dry cell cap housing a dry cell so as to be engaged with the other end of the handle portion, and an eccentric weight for producing vibration when the motor is actuated, thereby bringing the toothbrushing portion into vibration that is utilized to clean the teeth, the improvement comprising: a spacer disposed between the motor and the dry cell cap when the toothbrush is assembled, the spacer including a cylindrical main body, engagement arm portions formed at one end of the cylindrical main body toward the motor for engagement with the motor, and a guide groove portion formed on the periphery of the cylindrical main body so as to serve as a guide for the electric circuit-connecting terminal that intercommunicates the motor and the dry cell.

BRIEF DESCRIPTION OF THE DRAWINGS

FIG. 1 is a partially cutaway front view of an electrically driven toothbrush pursuant to a first embodiment of the invention, and wherein:

FIG. 27 is a schematic view, showing the flexibility of an operating portion of the switch lever;

FIG. 28 are schematic cross-sectional views illustrating the dry cell cap in the process of being assembled, in which FIG. 28A is a schematic cross-sectional view showing an action before the operating portion of the switch lever is inserted into a hole portion of the dry cell cap, FIG. 28B is a schematic cross-sectional view showing an action at the moment when the operating portion is inserted into the hole portion, FIG. 28C is a schematic cross-sectional view showing an action after the operating portion is inserted through the hole portion, FIG. 28D is a schematic cross-sectional view showing an action at the moment when a revolving shaft portion of the switch lever is moved through the hole portion, and FIG. 28E is a schematic cross-sectional view showing the dry cell cap when attachment of the switch lever is complete;

FIG. 29 illustrates a first terminal member, in which

FIG. 30 illustrates a portion of the first terminal member, in which

FIG. 33 illustrates a second terminal member, in which

FIG. 34 illustrates a portion of the second terminal member, in which

FIG. 35 illustrates another portion of the second terminal member, in which

FIG. 41 illustrates on/off actions of the switch lever, in which

FIG. 43 illustrates the on/off actions of the switch lever, in which

FIG. 48 are schematic views illustrating a second embodiment, in which

FIG. 49 is a perspective view showing assembly of an electrically driven toothbrush pursuant to a third embodiment of the invention, wherein:

FIG. 66 are schematic cross-sectional views illustrating the dry cell cap in the process of being assembled, in which

FIG. 70 illustrates a first terminal, in which

FIG. 71 illustrates a second terminal, in which

FIG. 72 illustrates a portion of the second terminal, in which

FIG. 73 illustrates another portion of the second terminal, in which

FIG. 74 is a schematic view showing the first terminal and a motor before the former is attached to the latter in engagement therewith;

FIG. 75 is a schematic view showing the first terminal and the motor after the former is attached to the latter in engagement therewith;

FIG. 76 is a schematic view showing the second terminal in a state of being connected to the first terminal that is attached to the motor in engagement therewith;

FIG. 77 illustrates on/off actions of the switch lever, in which FIG. 77A is a schematic plan view showing the switch lever and FIG. 77B is a schematic view showing how the operating portion of the switch lever undergoes movement in dependence upon the on/off actions of the switch lever;

FIG. 79 illustrates the on/off actions of the switch lever, in which

FIG. 83 illustrates the motor and the spacer in a state of being engaged with one another, in which

DETAILED DESCRIPTION

FIGS. 1–48

One embodiment of the present invention will be described in detail with reference to FIGS. 1–47.

Figure 1:
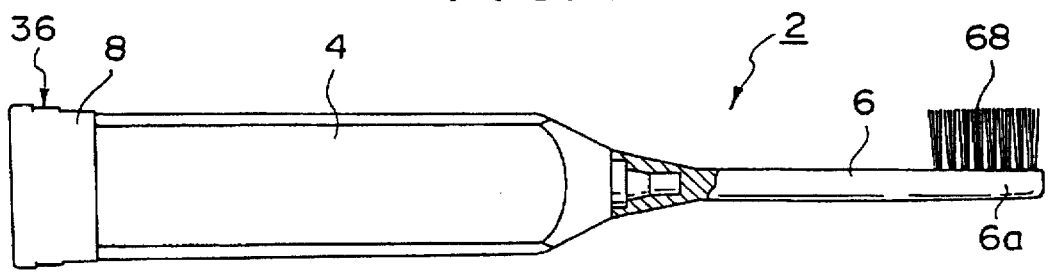
Figure 2:
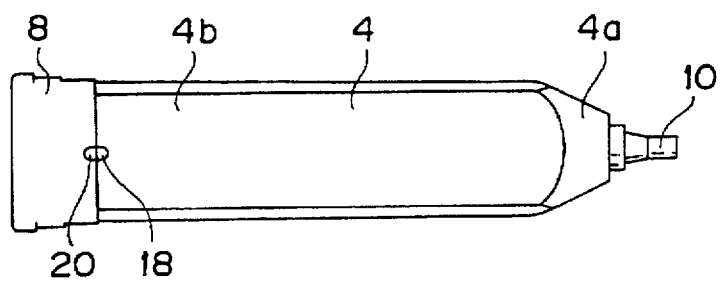
FIG. 2 is a rear view of the toothbrush without a toothbrushing portion.
Figure 3:
FIG. 3 is a bottom view of the toothbrush without the toothbrushing portion.
Figure 4:
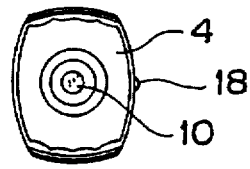
FIG. 4 is a right side view of the toothbrush without the toothbrushing portion.
Figure 5:
FIG. 5 is a left side view of the toothbrush without the toothbrushing portion.
Figure 6:
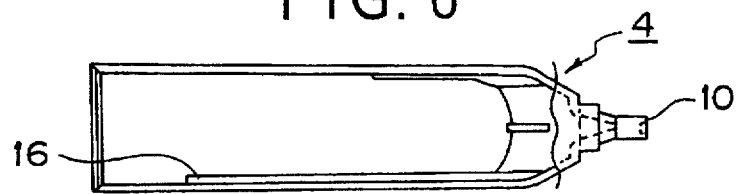
FIG. 6 is a schematic cross-sectional front view of a handle portion of the toothbrush.
Figure 7:
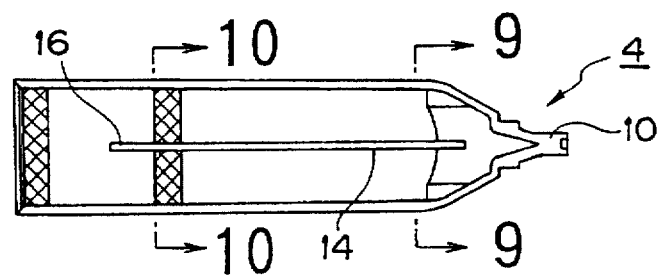
FIG. 7 is a schematic cross-sectional plan view of the handle portion.
Figure 8:
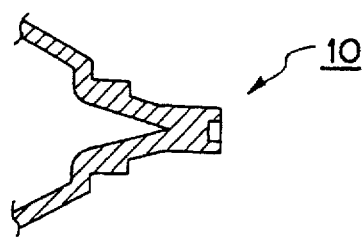
FIG. 8 is a schematic enlarged cross-sectional view of an engagement-protruding portion of the handle portion.
Figure 9:
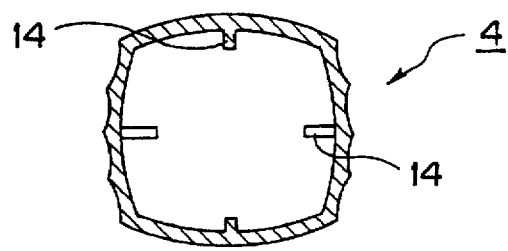
FIG. 9 is an enlarged cross-sectional view taken along line 9—9 of FIG. 7.

In FIG. 1, 2 denotes a vibration type of electrically driven toothbrush; 4 an elongate hollow handle portion; 6 a toothbrushing portion; and 8 a dry cell cap which is of a tubular shape having a bottom or end wall.

The handle portion 4 is formed from a resin material such as plastics so as to have a substantially rectangular-shaped hollow cross-section in which a pair of opposing surfaces is defined with waveforms. At one end 4a of the handle portion 4, where the toothbrushing portion 6 is engaged with the handle portion 4, there is formed an engagement-protruding shaft portion 10 adapted for mounting the toothbrushing portion 6. Further, the handle portion 4 has the dry cell cap 8 engaged with the other end 4b thereof. The cap 8 houses a dry cell 28 as described hereinafter.

Figure 10:
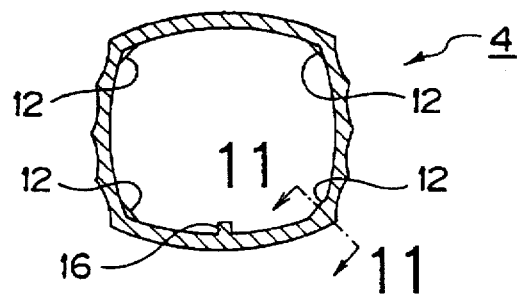
FIG. 10 is an enlarged cross-sectional view taken along line 10—10 of FIG. 7.
Figure 11:
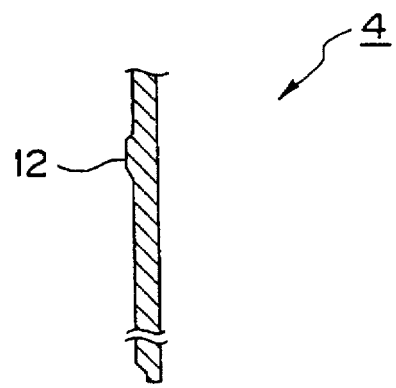
FIG. 11 is an enlarged cross-sectional view taken along line 11-1 of FIG. 10.
Figure 12:
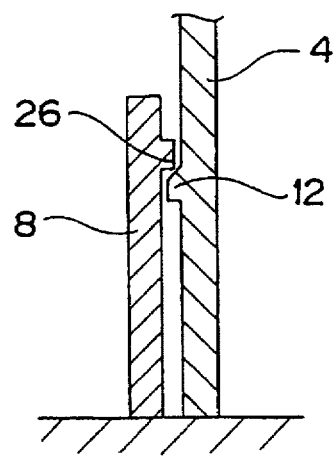
FIG. 12 is a schematic enlarged cross-sectional view, showing the handle portion and a dry cell cap in a state of engagement with one another.
Figure 13:
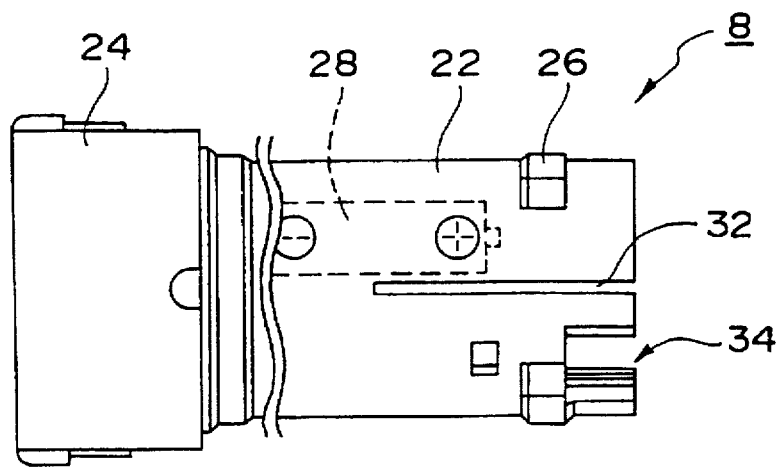
FIG. 13 is a front view of the dry cell cap.
Figure 14:
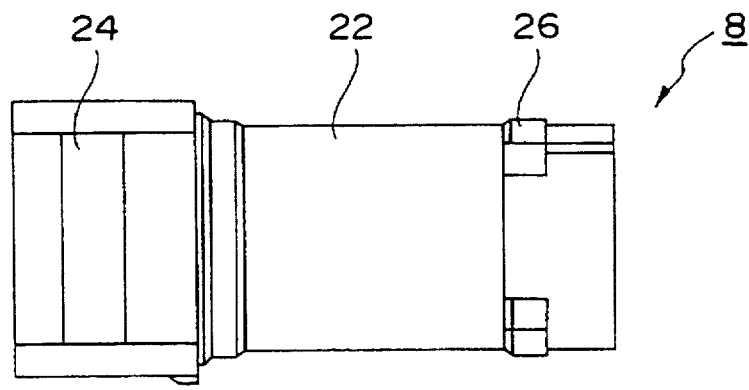
FIG. 14 is a bottom view of the dry cell cap.
Figure 15:
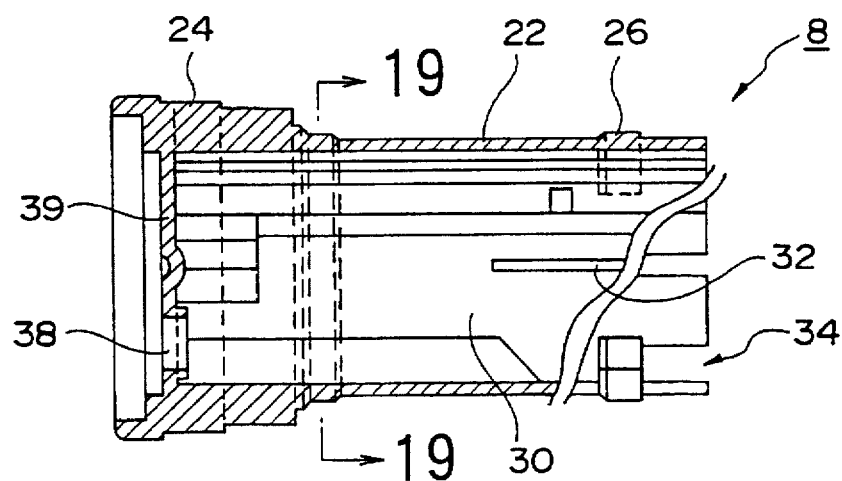
FIG. 15 is a central transverse cross-sectional view of FIG. 13.

Referring to FIGS. 10 through 12, the handle portion 4 is shown having thickening portions 12 therein. The thickening portions 12 are located at inner square corners of the handle portion 4 and at a predetermined distance from one end thereof so as to be engaged with engagement protrusions 26 (FIG. 12) of the cap 8, thereby releasably fixing the cap 8 to the handle portion 4. The engagement protrusions 26 are described hereinafter.

The handle portion 4 has retaining protrusions 14 (FIGS. 7 and 9) defined at the one end 4a thereof on the inner surface thereof for holding a motor 56 (FIG. 47) in position. The motor 56 is described hereinafter. The handle portion 4 further has a positioning protrusion 16 (FIG. 7) defined at the other end 4b thereof on the inner surface thereof. The positioning protrusion 16 is engaged with a slit 32 (FIG. 13) of the cap 8 for holding the cap 8 in position. The slit 32 is described hereinafter.

Furthermore, the handle portion 4 has a first protrusion 18 (FIG. 2) provided at the other end 4b thereof on the outer periphery thereof for matching a second protrusion 20 that is formed on the cap 8, thereby serving to effect positioning when the cap 8 is engaged with the handle portion 4. The first protrusion 18 is arcuate in cross-section.

The dry cell cap 8 is formed from a resin material such as plastics, and includes a sleevelike cylindrical engagement surface portion 22 and a handgrip 24, as illustrated in FIGS. 13 through 18. The engagement surface portion 22 is held in engagement within the other end 4b of the handle portion 4. The handgrip 24 enables release of such engagement when the dry cell 28 is replaced, thereby enabling the cap 8 to be removed from the handle portion 4.

In addition, the engagement surface portion 22 has the engagement protrusions 26 formed on the outer surface thereof for engagement with the thickening portions 12 of the handle portion 4. Further, a space or chamber 30 is defined by the inner surface of the engagement surface portion 22 for housing the dry cell 28.

As respectively illustrated in FIGS. 13, 15, 44, and 45, the engagement surface portion 22 is formed with the slit 32 which is cut axially away from an open end of the engagement surface portion 22 toward the handgrip 24 by a distance of approximately a third of the entire length. When the cap 8 is engaged with the handle portion 4, the slit functions to fix the cap 8 in position by being engaged with the positioning protrusion (i.e. rib) 16 of the handle portion 4. Further, a cutout portion 34 is defined at the open end portion of the engagement surface portion 22.

Figure 21:
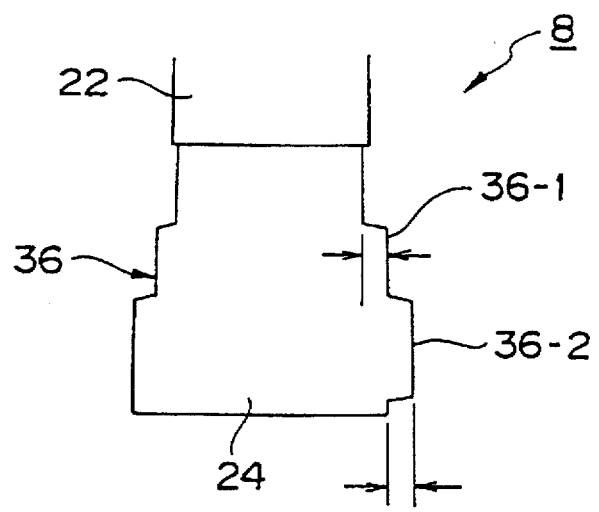
FIG. 21 is a schematic view showing the staged portion formed at a discharging portion of the dry cell cap.

Referring to FIG. 21, the handgrip 24 is shown having a staged portion 36 formed on the pair of opposite surfaces thereof on the outer periphery thereof. The staged portion 36 increases in size in a stepped manner from the side of the engagement surface portion 22 toward the outer or free end of the handgrip 24. The staged portion 36 includes first and second stepped portions 36-1 and 36-2. The first stepped portion 36-1 increases in size from the side of engagement surface portion 22 toward the handgrip 24. The second stepped portion 36-2 increases in size from the first stepped portion 36-1 toward the handgrip 24.

The cap 8 has a hole 38 (FIG. 16) provided through an end wall 39 thereof. The cap 8 is further provided with a switch lever 40 (FIG. 28) which is engaged with the hole 38 for switching the motor 56 on and off.

The switch lever 40 (FIG. 23) is formed by: a manipulation control portion 42 which is positioned outside the dry cell cap 8 when engaged with the cap 8; a revolving shaft portion 44 fixedly attached to the manipulation control portion 42 and tightly fitted in the hole 38; a spherical operating portion 46 situated inside the cap 8; and a L-shaped lever portion 48 connected between the operating portion 46 and the revolving shaft portion 44. These components are formed integrally as a flexible one-piece member.

More specifically, the manipulation control portion 42 includes a manipulation plate 50 and a control portion 52, as shown in FIGS. 23 through 26. The manipulation plate 50 is in the form of an arrow. The control portion 52 is provided at a central portion of the manipulation plate 50, and protrudes outwardly away from the cap 8, i.e., in the downward direction of FIG. 23.

Figure 23:
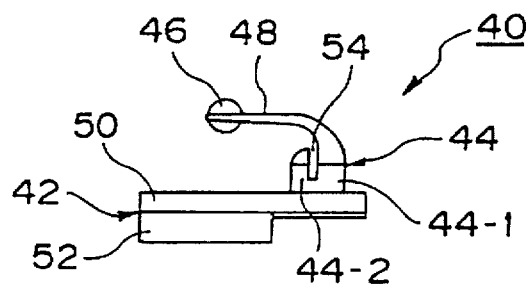
FIG. 23 is a front view of a switch lever.
Figure 24:
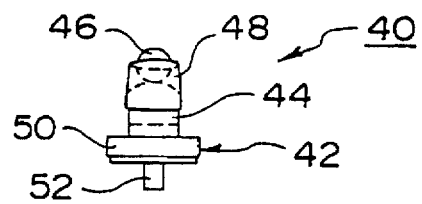
FIG. 24 is a right side view of the switch lever.
Figure 25:
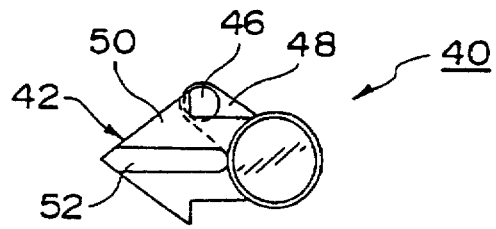
FIG. 25 is a bottom view of the switch lever.
Figure 26:
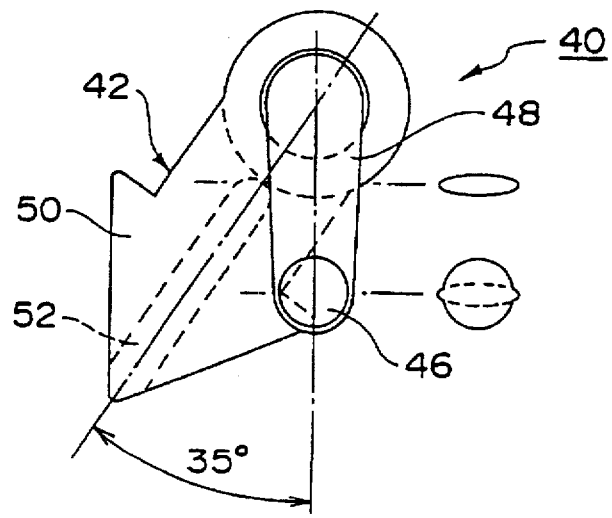
FIG. 26 is an enlarged view of the switch lever.
Figure 29A:
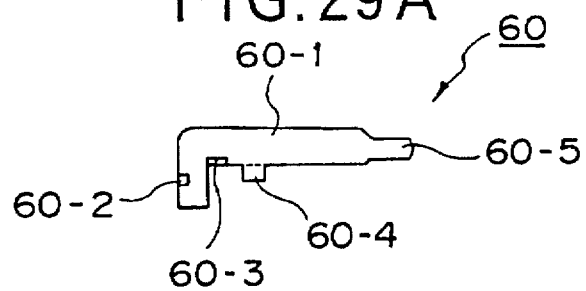
FIG. 29A is a plan view and FIG. 29B is a front view thereof.
Figure 29B:
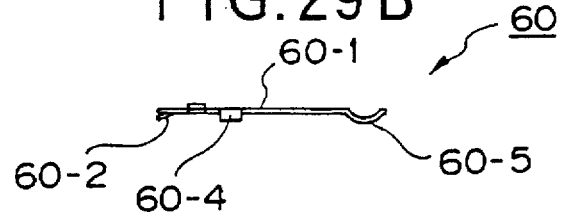
Figures 30A, 30B:
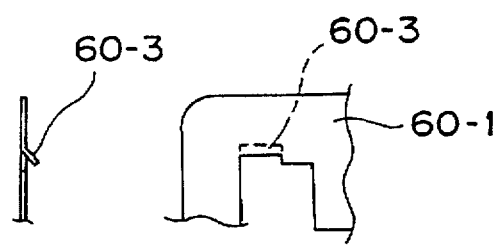
FIG. 30A is an enlarged right side view showing a second cut and raised portion.
FIG. 30B is an enlarged front view showing the second cut and raised portion.
Figure 31:
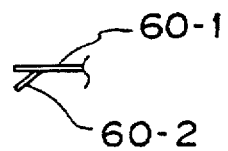
FIG. 31 is an enlarged front view showing a first cut and raised portion of the first terminal member.
Figure 32:
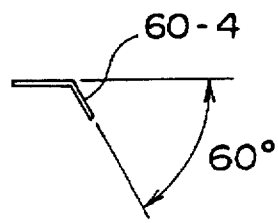
FIG. 32 is an enlarged left side view showing a bent portion of the first terminal member.

As shown in FIG. 23, the revolving shaft portion 44 is disposed vertically on the manipulation plate 50. In addition, the revolving shaft portion 44 is formed so as to be slightly larger in outer diameter than the hole 38. Further, in order to divide an end portion of the revolving shaft portion 44 in the inward direction of the dry cell cap 8 into a main shaft portion 44-1 and a subshaft portion 44-2, a slit 54 is formed in the inward direction of the dry cell cap 8, or downwardly from the top of FIG. 23.

The lever portion 48 is connected at one end to the main shaft portion 44-1 and at the other end to the spherical operating portion 46.

The switch lever 40 is formed integrally as a flexible one-piece member by being formed of a suitable material such as a plastics, one example being polyacetal (POM) resin.

Yet further, an electric circuit-connecting terminal 58 (FIG. 42) is provided for connecting the motor 56 and the dry cell 28 in communication with one another in order to drive the motor 56. The electric circuit-connecting terminal 58 is formed by: a first terminal 60 whose one end contacts the motor 56, while the other end thereof extends toward the dry cell 28; and a second terminal 62 whose one end contacts the other end of the first terminal 60, while the other end of the second terminal 62 communicates with the switch lever 40, extending over the dry cell 28.

Referring now to FIGS. 29 through 32, the first terminal 60 is shown including the following: a platelike main body 60-1 that is an electrically conductive, metallic member formed into a L-shaped configuration; a first cut and raised portion (i.e. a tab) 60-2 formed on part of a shorter leg of the main body 60-1; a second cut and raised portion (i.e. a tab) 60-3 formed on a longer leg of the main body 60-1 and adjacent to a location where the longer and shorter legs of the main body 60-1 join; a sideward projecting bent portion or tab 60-4 formed adjacent to the second cut and raised portion 60-3; and a curved portion 60-5 formed at a free end portion of the longer leg of the main body 60-1, i.e., at an end portion of the main body 60-1 which extends toward the dry cell 28.

Figures 33A, 33B:
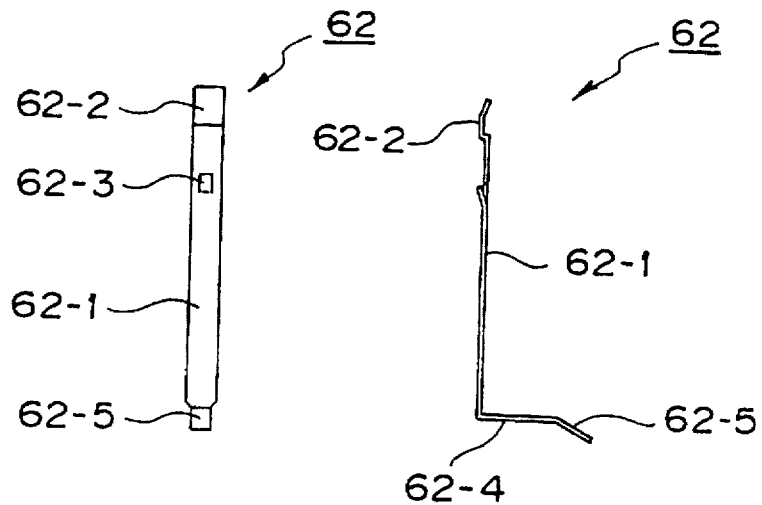
FIG. 33A is a left side view and FIG. 33B is a front view thereof.
Figures 34A, 34B:
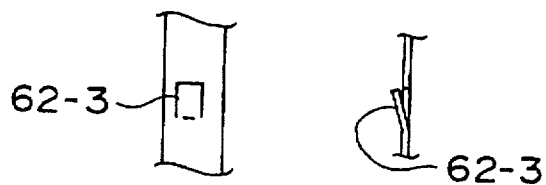
FIG. 34A is an enlarged left side view showing a cut and raised portion.
FIG. 34B is an enlarged front view showing the cut and raised portion.
Figures 35A, 35B:
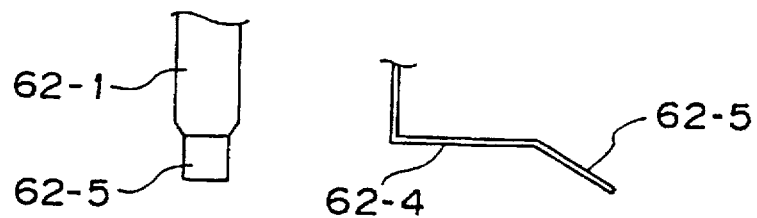
FIG. 35A is an enlarged left side view showing a swinging end portion.
FIG. 35B is an enlarged front view showing the swinging end portion.
Figure 35C:
FIG. 35C is an enlarged plan view showing the swinging end portion.

As illustrated in FIGS. 33 through 35, the second terminal 62 includes the following: a platelike main body 62-1 that is an electrically conductive, metallic member bent into a L-shape in cross-section; a deformed contact portion 62-2 defined at one end portion (i.e. a free end) of the main body 62-1, the contact portion 62-2 having a shape to contact the curved portion 60-5 of the first terminal 60; a cut and raised portion or tab 62-3 formed substantially midway along the main body 62-1; a bent portion 62-4 formed by the other end portion of the main body 62-1 and being slightly decreased in width dimension and further being bent into a L-shape in cross-section; and a swinging end portion 62-5 formed at a free end of the bent portion 62-4, the swinging end portion 62-5 being bent toward the switch lever 40, i.e., in the downward direction of both FIG. 33B and FIG. 35B.

The platelike main body 62-1 of the second terminal 62 has resilient force imparted thereto. The main body 62-1 is thereby constructed to spring back to the predetermined L-shape in cross-section when no external forces are exerted thereon.

For example, any motor conforming to a specification of 1.5 volts and 7,000 rpm is normally used as the motor 56. In this case, the vibration frequency ranges from about 6,000 to about 8,000 cycle per minute (cpm), e.g., typically about 7,000 cpm. For reference only, in order to establish 7,000 rpm as the speed specification of the motor 56, a determination is made in light of coil diameter, number of coil winding, and voltage.

Figure 16:
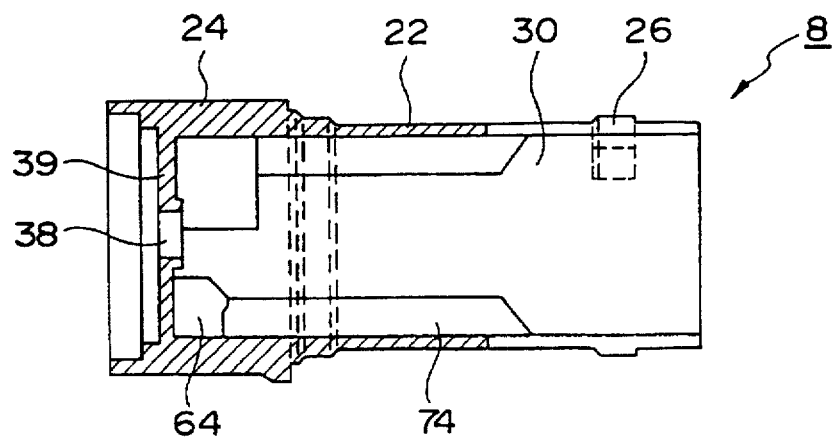
FIG. 16 is a central transverse cross-sectional view of FIG. 14.
Figure 17:
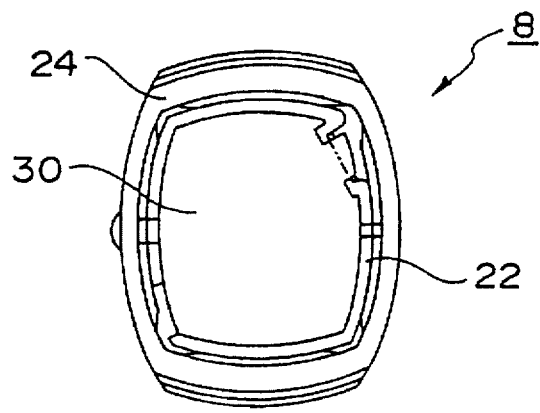
FIG. 17 is a right side view of the dry cell cap.
Figure 18:
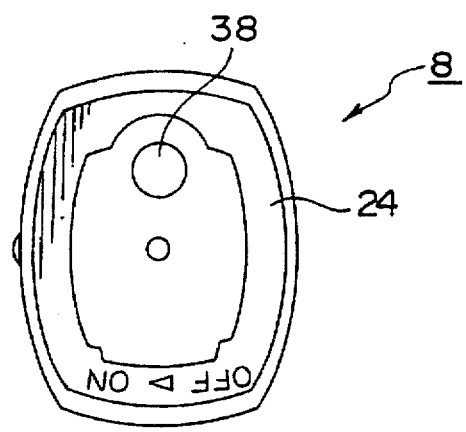
FIG. 18 is a left side view of the dry cell cap.
Figure 19:
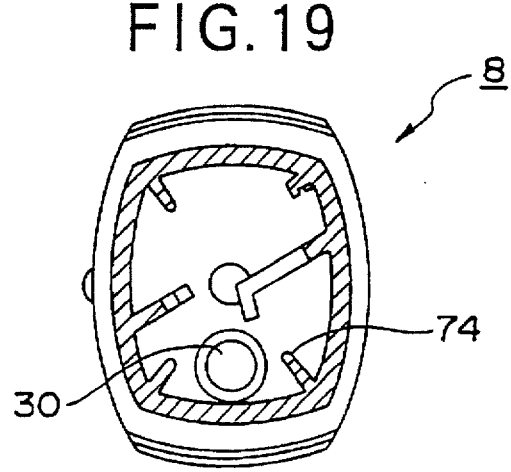
FIG. 19 is a cross-sectional view taken along line 19—19 of FIG. 15.
Figure 20:
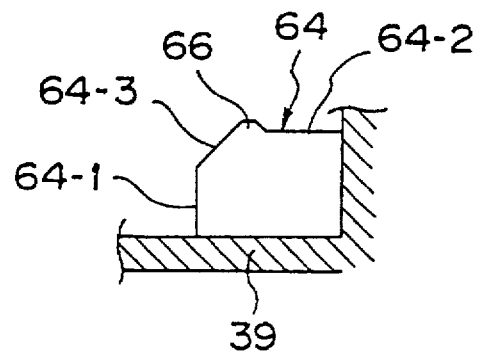
FIG. 20 is a schematic view showing a staged portion of the dry cell cap.

Turning now to FIGS. 16 and 20, a scuff plate 64 is shown formed integrally with the inner surface of the handgrip 24, when the dry cell cap 8 is formed from a resin material such as plastics. As illustrated in FIG. 20, the scuff plate 64 includes the following: a wall surface portion 64-1 rising from the bottom 39 of the dry cell cap 8 toward the handle portion 4; a planar surface portion 64-2 extending parallel to the bottom or end wall 39; and a slanted surface portion 64-3 having the wall surface portion 64-1 and the planar surface portion 64-2 in communication with one another. In addition, a convex portion 66, which protrudes toward the handle portion 4, is defined between the planar surface portion 64-2 and the slanted surface portion 64-3.

Reference numeral 68 (FIG. 1) denotes bristles made of for example pig bristles or linear plastic members, either of which are disposed at one end 6a of the toothbrushing portion 6; 70 (FIGS. 36–38) a revolving shaft of the motor 56; 72 an eccentric weight mounted eccentrically on the revolving shaft 70 for producing vibration with the revolving shaft 70 when the eccentric weight 72 is driven by the motor 56; and 74 (FIGS. 16 and 19) a projection or rib formed on the inner surface of the dry cell cap 8 for retaining the dry cell 28.

The operation of the above-described invention will now be described.

Figure 22:
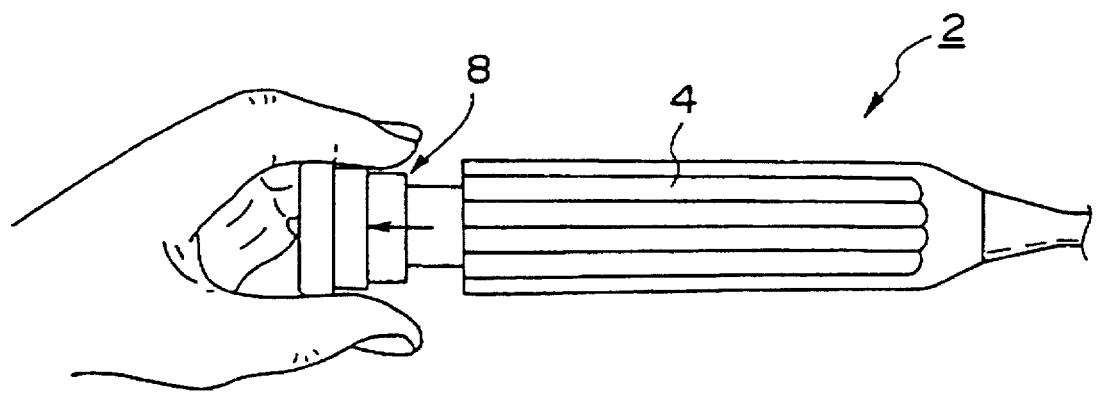
FIG. 22 is a schematic view illustrating the dry cell cap in a state of being removed from the handle portion.

As shown in FIG. 22, in order to detach dry cell cap 8 from handle portion 4 of the aforesaid electrically driven toothbrush 2, it is only necessary to pull the dry cell cap 8 out of the handle portion 4 through the aid of a staged portion 36 that is formed on the outer periphery of the cap 8, thereby releasing a state of engagement between thickening portions or detents 12 of the handle portion 4 and engagement protrusions 26 of the cap 8.

Conversely, when sleeve part 22 of cap 8 is inserted into the handle portion 4, the handle portion 4 and the cap 8 are arranged in alignment with one another using first and second protrusions 18 and 20 which lie on the respective outer peripheries of the handle portion 4 and dry cell cap 8. Then, slit 32 of the cap 8 is brought into engagement with the positioning protrusion or rib 16 of the handle portion 4, thereby slidably inserting the cap 8 into the handle portion 4.

When the thickening portions 12 are engaged with the engagement protrusions 26, a distal end portion of the sleeve part 22 is slightly reduced in dimension as a result of the cap 8 being defined with the slit 32 therein. Consequently, easy engagement is achievable.

For assembly of the dry cell cap 8, the flexibility of the lever portion 48 of the switch lever 40 is utilized. As shown in FIG. 28A through FIG. 28D, the operating portion 46 of the switch lever 40 is inserted into the cap 8 through the hole 38. When the insertion is complete, the revolving shaft portion 44 of the switch lever 40 is fitted in the hole 38 in a watertight manner with the aid of the memory (i.e. flexibility) of the revolving shaft portion 44, as illustrated in FIG. 28E.

More specifically, as illustrated in FIG. 28D, the main shaft portion 44-1 and sub-shaft portion 44-2 of the revolving shaft portion 44 are compressed toward one another in the hole 38 after the operating portion 46 is inserted through the hole 38. The slit 54 causes the sub-shaft portion 44-2 to be closer to the main shaft portion 44-1 while these two shaft portions are moved through the hole 38. After the shaft portions 44-1 and 44-2 are driven through the hole 38, the sub-shaft portion 44-2 is again spaced apart from the main shaft portion 44-1 by the returning elastic force of the revolving shaft portion 44. As a result, the revolving shaft portion 44 is retained in a watertight manner.

Figure 36:
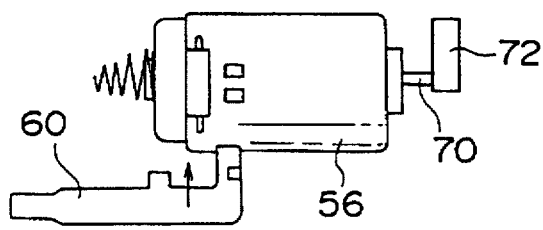
FIG. 36 is a schematic view showing the first terminal member and a motor before the former is attached to the latter in engagement therewith.
Figure 37:
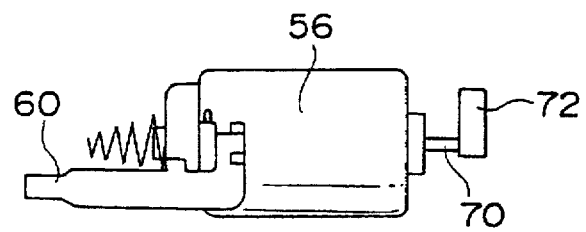
FIG. 37 is a schematic view showing the first terminal member and the motor after the former is attached to the later in engagement therewith.

Next, for the attachment of the electric circuit-connecting terminal 58, the first terminal 60 is initially attached to the motor 56 in engagement therewith through the utilization of the first tab 60-2 at one end of the first terminal 60, as illustrated in FIGS. 36 and 37. Then, the contact portion 62-2, which is one end portion of the second terminal 62, is connected to the curved portion 60-5 which is the other end portion of the first terminal 60.

Figure 38:
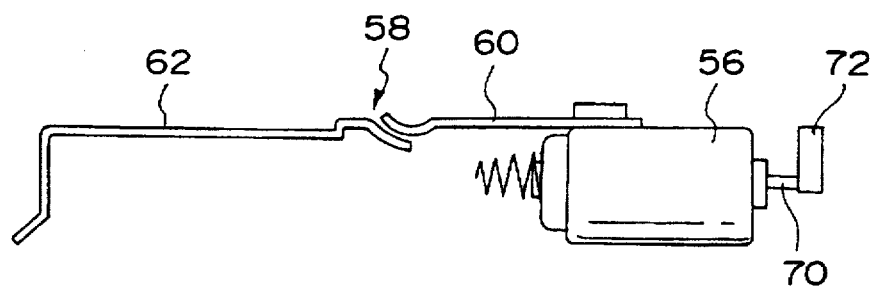
FIG. 38 is a schematic view showing the second terminal member in a state of being communicated to the first terminal member that is attached to the motor in engagement therewith.
Figure 39:
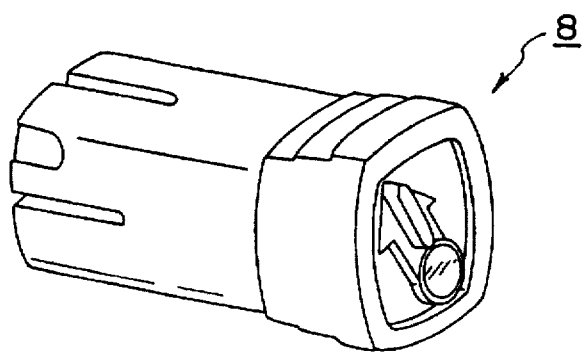
FIG. 39 is a schematic perspective view illustrating the dry cell cap.
Figure 40:
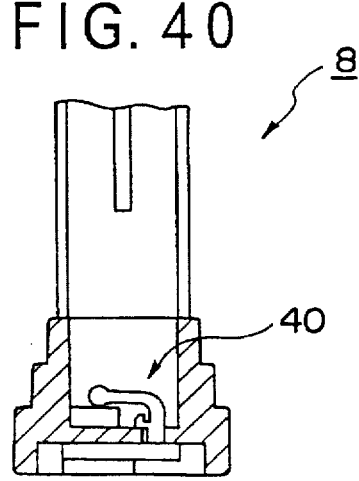
FIG. 40 is a schematic cross-sectional view showing the dry cell cap in a state of being fitted with the switch lever.
Figures 41A, 41B:
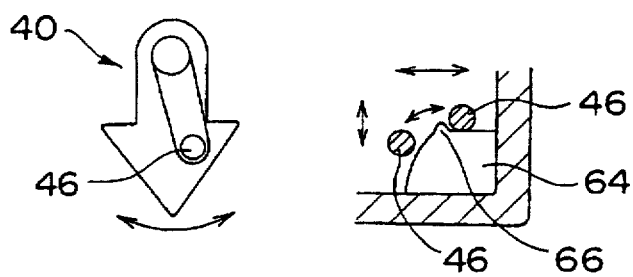
FIG. 41A is a schematic plan view showing the switch lever.
FIG. 41B is a schematic view showing how the operating portion of the switch lever is moved in dependence upon the on/off actions of the switch lever.

At this time, the curved portion 60-5 and the contact portion 62-2 are insecurely connected together as shown in FIG. 38. However, it is possible to insure a positive connection between the curved portion 60-5 and the contact portion 62-2. That is, after the second terminal 62 is disposed on the inner surface of the cap 8, the cap 8 is inserted into the handle portion 4; and the curved portion 60-5 and the contact portion 62-2 are thereby brought into contact with one another.

Figure 42:
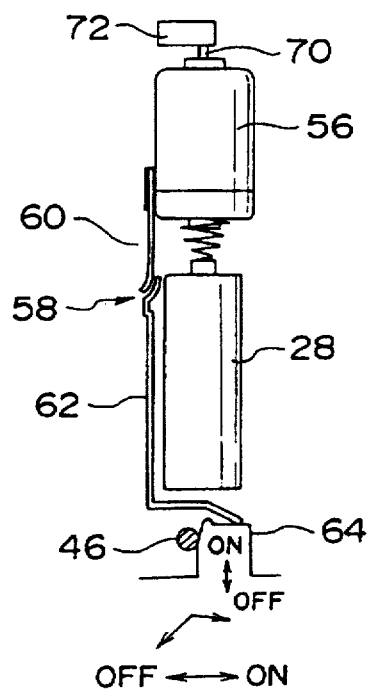
FIG. 42 is a schematic view illustrating an electric circuit-connecting terminal for use in the toothbrush.
Figure 46:
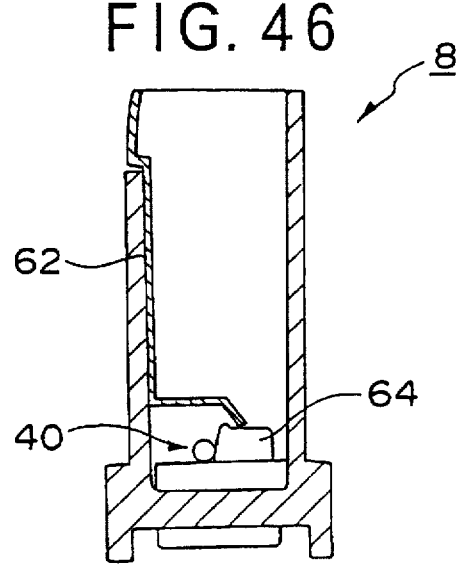
FIG. 46 is a schematic cross-sectional view of the dry cell cap.
Figure 47:
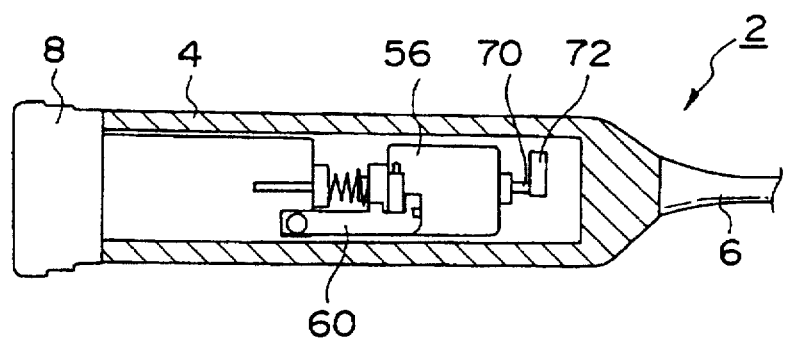
FIG. 47 is a schematic cross-sectional view showing the electrically driven toothbrush.

As illustrated in FIGS. 42 and 46, the second terminal 62 is positioned on the inner surface of the dry cell cap 8; and the bent portion 62-4 and the swinging end portion 62-5, both of which form the other end portion of the second terminal 62, are located adjacent the negative terminal of the dry cell 28.

Figures 43A, 43B, 43C:
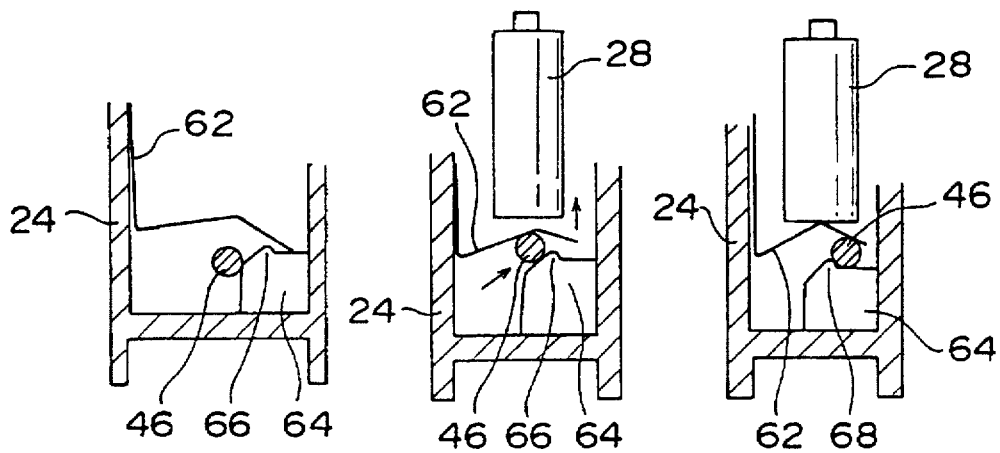
FIG. 43A is a schematic cross-sectional view showing the operating portion of the switch lever when the switch lever is off.
FIG. 43B is a schematic cross-sectional view showing the aforesaid operating portion when the switch lever starts the on action.
FIG. 43C is a schematic cross-sectional view showing the aforesaid operating portion when the on action is complete.
Figure 44:
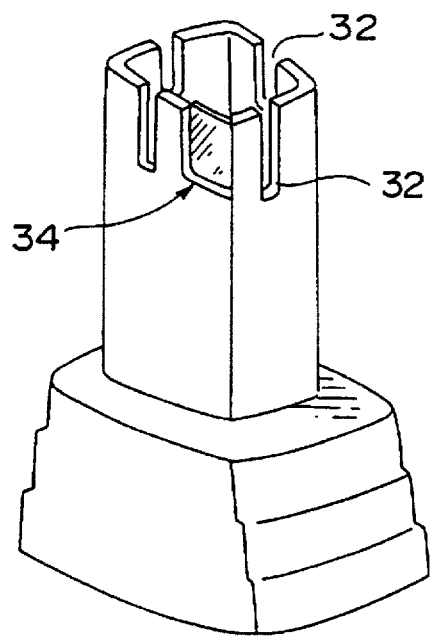
FIG. 44 is a schematic perspective view of the dry cell cap.
Figure 45:
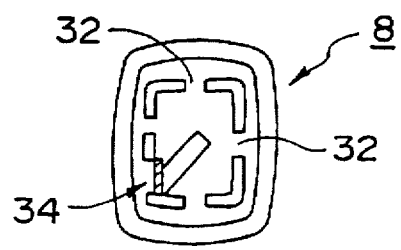
FIG. 45 is a plan view of the dry cell cap when viewed from the top of FIG. 44.

When the manipulation control portion 42 of the switch lever 40 as attached to the cell cap 8 is held and turned about the revolving shaft portion 44 so as to provide an "on" action, the operating portion 46 of the switch lever 40 is caused to slide along the scuff plate 64, as illustrated in FIG. 43. That is, the operating portion 46 is first moved to the convex portion 66 along the wall surface portion 64-1 and the slanted surface portion 64-3. After riding over the convex portion 66, the operating portion 46 reaches the planar surface portion 64-2, thereby thrusting the swinging end portion 62-5 upward. As a result, the other end portion of the second terminal 62, or rather an intermediate portion between the bent portion 62-4 and the swinging end portion 62-5, is driven into contact with the negative terminal of the dry cell 28.

In a converse case of an "off" action, the manipulation control portion 42 of lever 40 is manually gripped and turned about the revolving shaft portion 44 in a reverse direction. Accordingly, the operating portion 46 is transferred from the planar surface portion 64-2 to the wall surface portion 64-1 by passing over the protrusion or convex portion 66 and the slanted surface portion 64-3. As a result, the intermediate portion of the second terminal 62 between the bent portion 62-4 and the swinging end portion 62-5 is lowered by its natural resilient restoring force, and is thus spaced apart from the negative terminal of the dry cell 28. In this way, the switch lever 40 provides an off action.

In conclusion, when the dry cell cap 8 is assembled, the operating portion 46 of the switch lever 40 can be inserted into the cap 8 through the opening or hole 38 of the cap 8 with the aid of the flexibility of the lever portion 48 of the switch lever 40, and upon completion of the above insertion, the revolving shaft portion 44 of the switch lever 40 can be fitted in the hole 38 in a watertight manner with the aid of the spring-back-force of the revolving shaft 44. As a result, the attachability of the switch lever 40 can be enhanced, which is advantageous in view of practical use.

In addition, since the switch lever 40 is integrally formed as a homogeneous one-piece flexible member, a low-priced switch structure which is easy to manufacture is achievable.

Furthermore, for attaching the electric circuit-connecting terminal 58, the first terminal 60 can be attached to the motor 56 in engagement therewith with the aid of the first tab portion 60-2 of the first terminal 60; and the contact portion 62-2 of the second terminal 62 is positioned on the curved portion 60-5 of the first terminal 60, whereby the curved portion 60-5 and the contact portion 62-2 can be brought into contact with one another when the cap 8 is inserted into the handle portion 4. As a result, it is possible to realize a simpler structured, electric circuit-connecting terminal 58 which is easy to fabricate at low cost.

Moreover, no separate urging means need be provided because the platelike main body 62-1 of the second terminal 62 has resilient force imparted thereto so as to spring back to a predetermined L-shape in cross-section when no external forces are exerted on the platelike main body 62-1. As a result, a simpler structure and downsized, electrically driven toothbrush 2 is achievable.

Furthermore, since the handgrip 24 of the dry cell cap 8 is provided with the stepped portion 36, the cap 8 is easily inserted into and removed from the handle portion 4. This is advantageous from the viewpoint of practical use.

Furthermore, as respectively disclosed in FIGS. 29 through 35, a radius is placed on each end portion of the first and second terminals 60 and 62. As a result, it is possible to enhance safety for replacement and maintenance or inspection of the cell 28.

Yet further, when a vibration frequency of the toothbrush 2 is established to be about 7,000 cpm, a high level of comfort can be obtained. Consequently, a feeling of discomfort is eliminated which would otherwise occur during toothbrushing.

Moreover, when the teeth are cleaned by the use of the toothbrush 2 having its vibration frequency established to be some 7,000 cpm, it is possible to improve tooth-cleaning effectiveness in removing plaque, dust or dirt, as compared with conventional toothbrushes. It is also possible to ensure sufficient cleaning effectiveness, contributing to reducing the time for cleaning the teeth. In addition, convenience of use is enhanced. Furthermore, massage of the gums as well as enhancement in the tooth-cleaning effectiveness during brushing can be provided simultaneously when vibration is conducted to the tips of the bristles 68 on the toothbrushing portion 6.

Figures 48A, 48B:
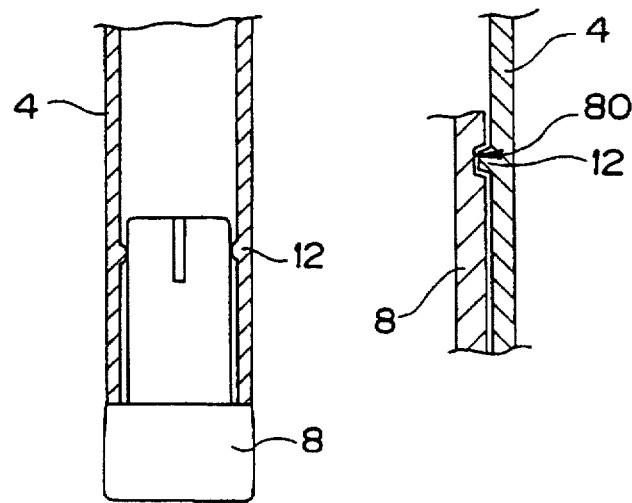
FIG. 48A is a schematic cross-sectional view showing a dry cell cap in a state of being attached to a handle portion.
FIG. 48B is a schematic enlarged cross-sectional view showing the handle portion and the dry cell cap in a state of being held in engagement with one another.

In the above-described embodiment of the invention, the thickening portions 12, which are formed on the handle portion 4, and the engagement protrusions 26 of a convex shape, which are formed on the cap 8, are designed to be brought into and out of engagement therebetween when the dry cell cap 8 is inserted into and withdrawn from the handle portion 4. Alternatively, as illustrated in FIGS. 48A and 48B, a concave or recess 80, e.g., may be formed on the outer periphery of the cap 8 so as to be forced into and out of engagement with each thickening portion 12 that is formed on the handle portion 4 to effect releasable securement of the cap 8 with the handle 4.

FIGS. 49–90

Another embodiment of the invention will now be described in detail with reference to FIGS. 49–90.

Figure 49:
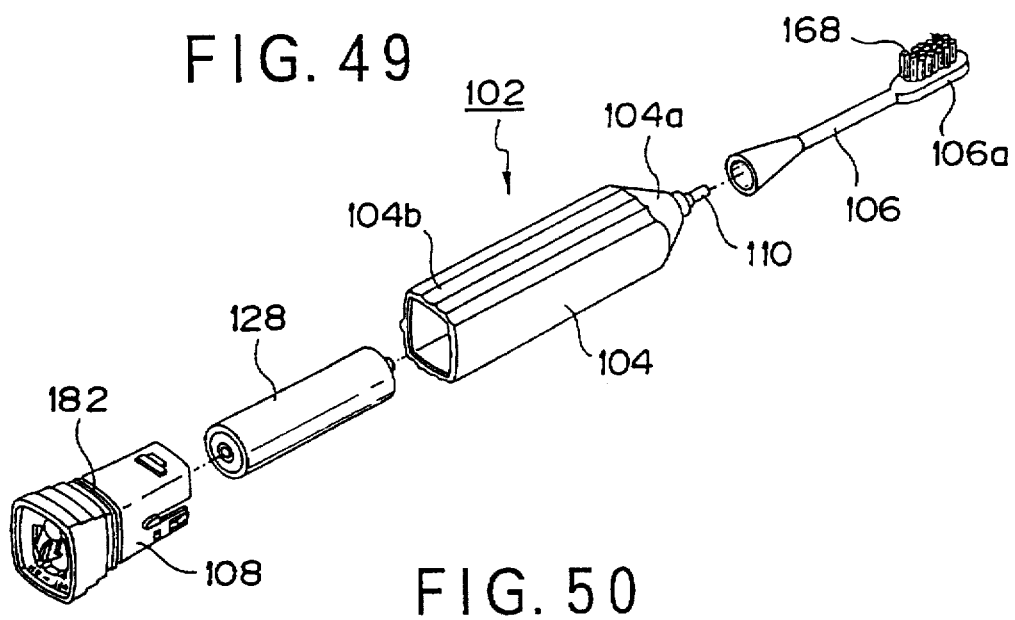
Figure 50:
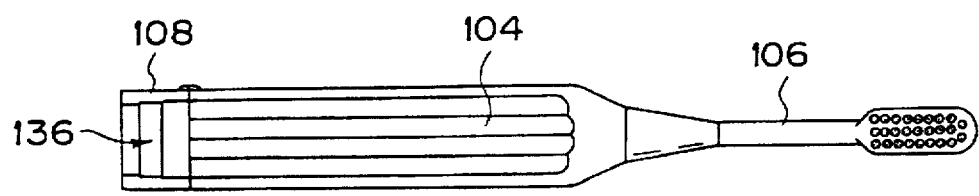
FIG. 50 is a front view showing the toothbrush.
Figure 51:
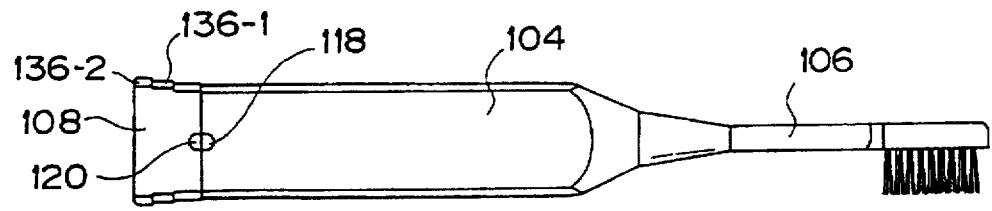
FIG. 51 is a left side view showing the toothbrush.
Figure 52:
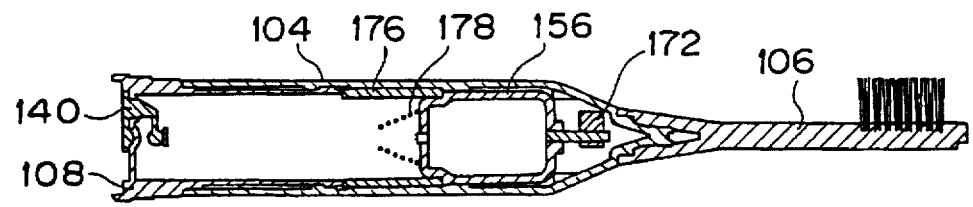
FIG. 52 is a central transverse cross-sectional view showing the toothbrush.
Figure 53:
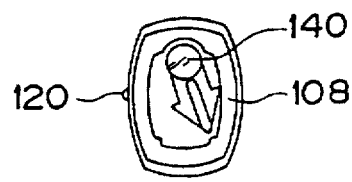
FIG. 53 is a bottom view showing the toothbrush.
Figure 54:
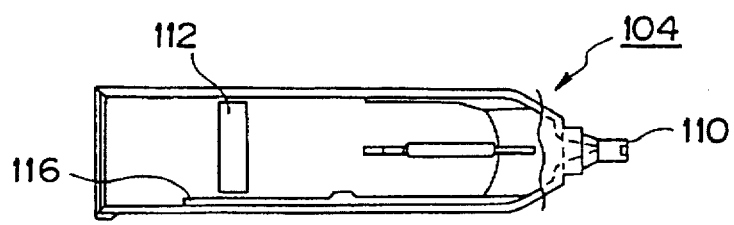
FIG. 54 is a schematic cross-sectional front view showing a handle portion of the toothbrush.
Figure 55:
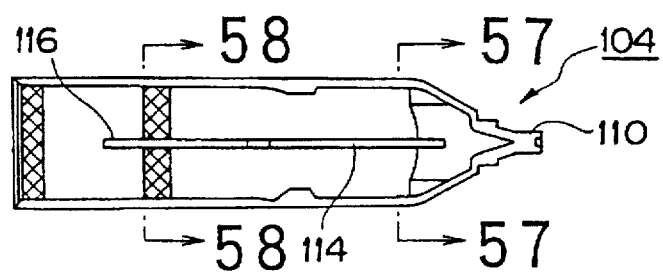
FIG. 55 is a schematic cross-sectional plan view showing the handle portion.
Figure 56:
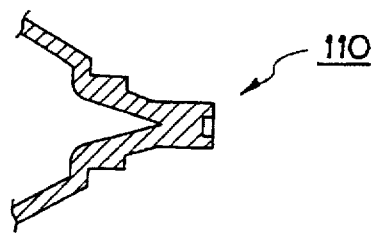
FIG. 56 is a schematic enlarged cross-sectional view showing an engagement-protruding portion of the handle portion.
Figure 57:
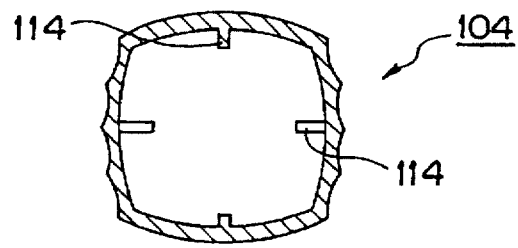
FIG. 57 is an enlarged cross-sectional view taken along line 57—57 of FIG. 55.

In FIG. 49, reference numeral 102 denotes a vibration type of electrically driven toothbrush; 104 a handle portion; 106 a toothbrushing portion; and 108 a dry cell cap which is formed into a cylindrical shape having a bottom or end wall.

The handle portion 104 is formed from a resin material such as plastics so as to have a substantially rectangular-shaped cross-section in which a pair of opposing surfaces is defined with waveforms. At one end 104a of the handle portion 104 where the toothbrushing portion 106 is engaged with the handle portion 104, there is formed an engagement-protruding portion 110 which is adapted for the toothbrushing portion 106. Further, the handle portion 104 has the dry cell cap 108 engaged with the other end 104b thereof. The dry cell cap 108 houses a dry cell 128 as described hereinafter.

Figure 58:
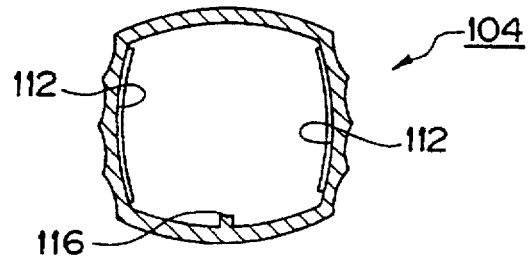
FIG. 58 is an enlarged cross-sectional view taken along line 58—58 of FIG. 55.
Figure 59:
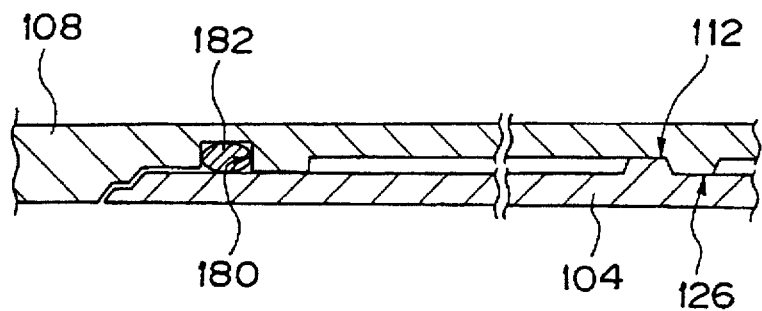
FIG. 59 is a schematic enlarged cross-sectional view showing the handle portion and a dry cell cap in a state of being engaged with one another.

Referring to FIGS. 58 and 59, the handle portion 104 is shown having first engagement-protrusions 112 at a predetermined height from the inner surface of the handle portion 104. The first engagement-protrusions 112 are band-shaped, and extend in a transverse direction of the handle portion 104 so as to be engaged with second engagement protrusions 126 of the dry cell cap 108, thereby fixing the cap 108 to the handle portion 104. The engagement protrusions 126 as described hereinafter are band-shaped, and extend in a transverse direction of the dry cell cap 118. The protrusions 112 effectively define an annular rim or flange which extends around the inner surface of the handle portion 104 and protrudes radially inwardly thereof, and similarly the protrusions 126 effectively define an annular rim or flange which surrounds the cap 108 and protrudes radially outwardly thereof.

The handle portion 104 has retaining protrusions 114 defined at the one end 104a thereof on the inner surface thereof for holding a motor 156 in position. The motor 156 will be described hereinafter. The handle portion 104 further has a positioning protrusion 116 defined at the other end 104b thereof on the inner surface thereof. The positioning protrusion 116 is adapted for engagement with a slit 132 of the dry cell cap 108 so as to fix the cap 108 in position. The slit 132 is described hereinafter.

Furthermore, the handle portion 104 has a first protrusion 118 provided at the other end 104b thereof on the outer periphery thereof. The first protrusion 118 is arcuate in cross-section, and is designed to match a second protrusion 120 that is formed on the dry cell cap 108, thereby serving to effect positioning when the dry cell cap 108 is engaged with the handle portion 104.

Figure 67:
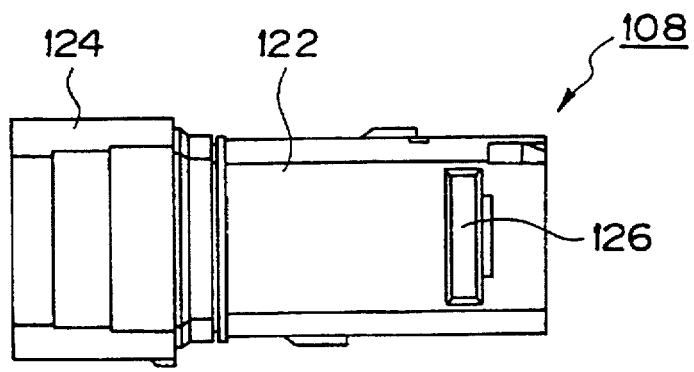
FIG. 67 is a bottom view showing the dry cell cap.
Figure 68:
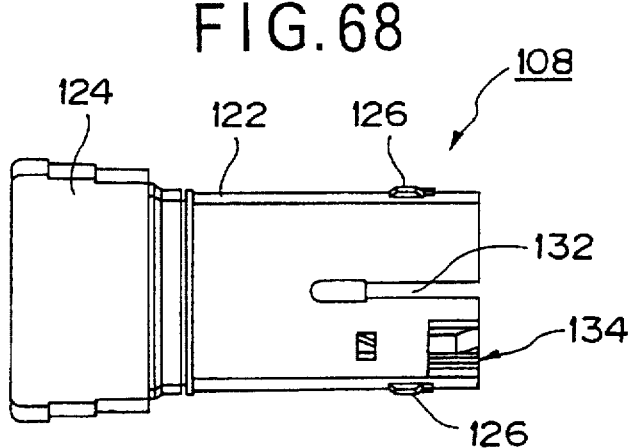
FIG. 68 is a front view showing the dry cell cap.
Figure 69:
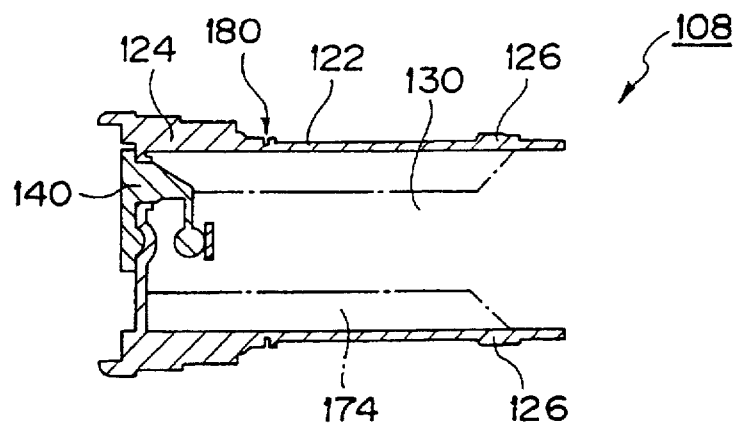
FIG. 69 is a central transverse cross-sectional view of FIG. 67.

The dry cell cap 108 is formed from a resin material such as plastics, and includes a cylindrical engagement surface portion 122 and a discharging handgrip 124, as illustrated in FIGS. 67–69. The engagement surface portion 122 is designed for engagement with the other end 104b of the handle portion 104. The discharging handgrip 124 serves to release such engagement in order to move the dry cell cap 108 out of the handle portion 104 when the dry cell 128 is replaced.

In addition, the engagement surface portion 122 has the engagement protrusions 126 formed on the outer surface thereof for engagement with the first engagement protrusions 112 of the handle portion 104. Further, a void space portion 130 for housing the dry cell 128 is defined by the inner surface of the engagement surface portion 122.

As illustrated in FIG. 68, the engagement surface portion 122 is formed with the slit 132 which is cut out from an open end of the engagement surface portion 122 toward the discharging handgrip 124 by a distance of about one third of the entire length. When the dry cell cap 108 is engaged with the handle portion 104, the slit 132 functions to fix the dry cell cap 108 in position by being engaged with the positioning protrusion 116 of the handle portion 104. Further, a cutout portion 134 is defined at the open end portion of the engagement surface portion 122.

Referring to FIGS. 67–69, the discharging handgrip 124 is shown having a staged portion 136 formed on a pair of opposing surfaces thereof on the outer periphery thereof. The staged portion 136 increases in size in a stepped manner from the engagement surface portion 122 toward the discharging handgrip 124. The staged portion 136 includes first and second staged portions 136-1 and 136-2. The first staged portion 136-1 increases in size from the engagement surface portion 122 toward the discharging handgrip 124. The second staged portion 136-2 further increases in size from the first staged portion 136-1 toward the discharging handgrip 124.

The dry cell cap 108 has a hole portion 138 provided through an end surface thereof. The dry cell cap 108 is further provided with a switch lever 140 which is engaged with the hole portion 138 for switching the aforesaid motor 156 on and off.

The switch lever 140 is formed by: a manipulation control portion 142 which is positioned outside the dry cell cap 108 when the switch lever 140 is engaged with the cap 108; a revolving shaft portion 144 fixedly attached to the manipulation control portion 142 and tightly fitted in the hole portion 138; a spherical operating portion 146 positioned inside the dry cell cap 108; and a lever portion 148 having the operating portion 146 and the revolving shaft portion 144 in communication with one another. These components of the switch lever 140 are formed integrally by a flexible one-piece member.

Figure 62:
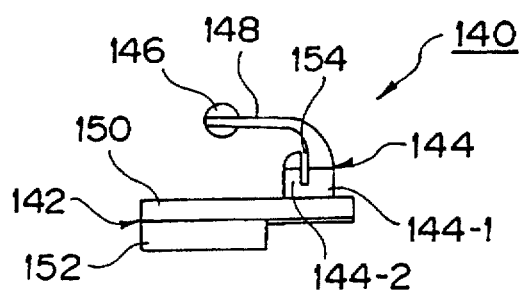
FIG. 62 is a front view showing a switch lever.
Figure 63:
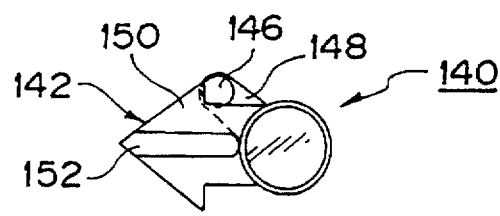
FIG. 63 is a bottom view showing the switch lever.
Figure 64:
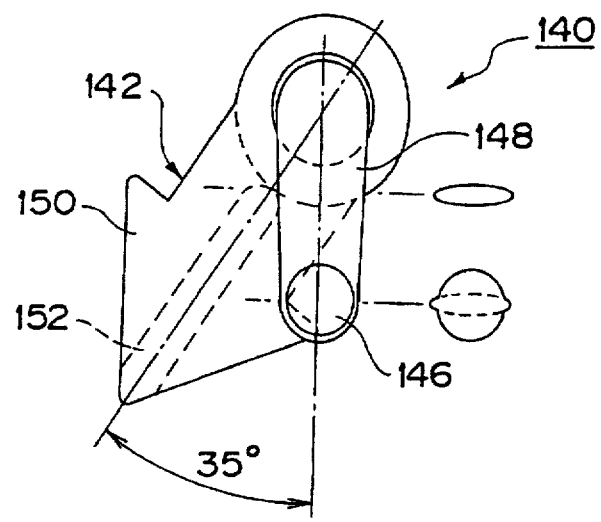
FIG. 64 is an enlarged view showing the switch lever.

As shown in FIGS. 62–64, the manipulation control portion 142 includes a manipulation plate 150 and a control portion 152. The manipulation plate 150 is in the form of an arrow. The control portion 152 is provided at a central portion of the manipulation plate 150, and protrudes outwardly from the dry cell cap 108, i.e., in the downward direction of FIG. 62.

As shown in FIG. 62, the revolving shaft portion 144 is disposed vertically on the manipulation plate 150. In addition, the revolving shaft portion 144 is formed so as to be slightly greater in outer diameter than the hole 138. Further, a slit 154 is formed in the inward direction of the dry cell cap 108, or downwardly from the top of the FIG. 62, thereby dividing an end portion of the revolving shaft portion 144 in the inward direction of the dry cell cap 108 into a main shaft portion 144-1 and a sub-shaft portion 144-2.

The lever portion 148 is connected at one end to the main shaft portion 144-1 and at the other end to the spherical operating portion 146.

The switch lever 140 is formed integrally by a flexible one-piece member such as polyacetal (POM) resin.

Further, in order to actuate the motor 156, an electric circuit-connecting terminal 158 is provided for having the motor 156 and the dry cell 128 in communication with one another. The terminal 158 is formed by: a first terminal 160 whose one end contacts the motor 156, while the other end thereof extends toward the dry cell 128; and a second terminal 162 whose one end contacts the other end of the first terminal 160, while the other end of the second terminal 162 communicates with the switch lever 140, extending over the dry cell 128.

Referring now to FIG. 69, the first terminal 160 is shown including the following: a platelike main body 160-1 of an electrically conductive, metallic member that is formed into a L-shaped configuration: a first cut and raised portion 160-2 formed on part of a shorter side of the main body 160-1; a second cut and raised portion 160-3 formed on a longer side of the main body 160-1 and adjacent to a location where the longer and shorter sides of the main body 160-1 communicate with one another; a bent portion 160-4 formed adjacent to the second cut and raised portion 160-3; and a curved portion 160-5 formed at an end portion of the longer side of the main body 160-1, i.e., at an end portion of the main body 160-1 which extends toward the dry cell 128.

Figures 71A, 71B:
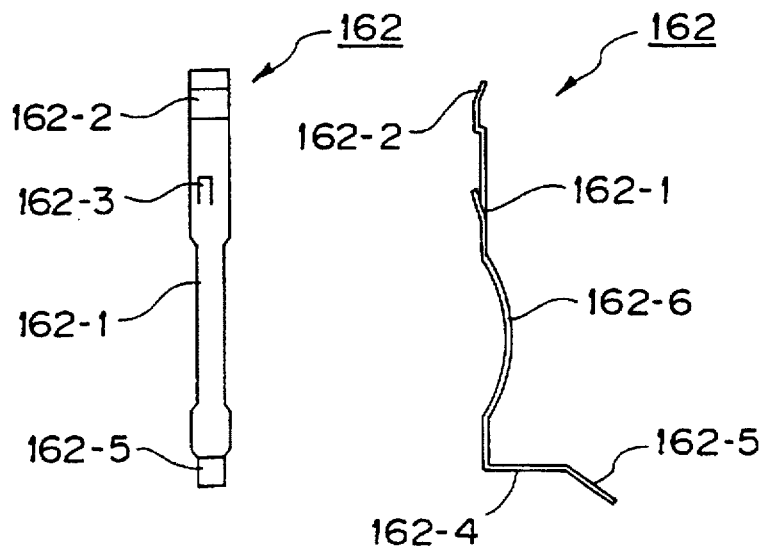
FIG. 71A is a left side view of the second terminal and FIG. 71B is a front view of the second terminal.
Figures 72A, 72B:
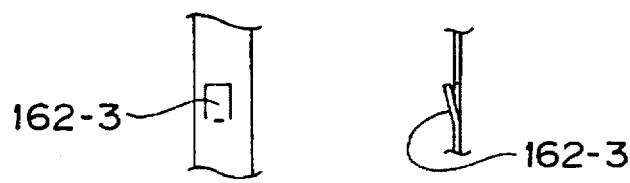
FIG. 72A is an enlarged left side view showing a cut and raised portion and FIG. 72B is an enlarged front view showing the cut and raised portion.
Figures 73A, 73B:
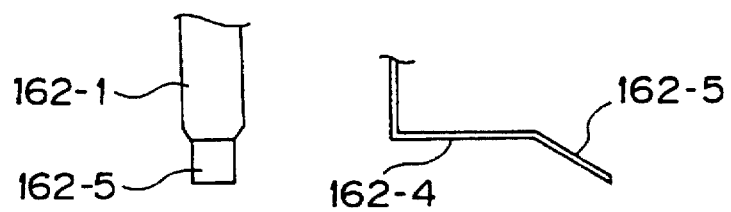
FIG. 73A is an enlarged left side view showing a swinging end portion.
FIG. 73B is an enlarged front view showing the swinging end portion.
Figure 73C:
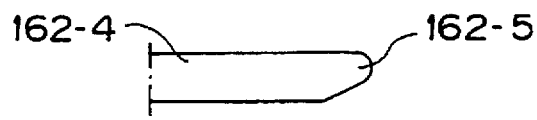
FIG. 73C is an enlarged plan view showing the swinging end portion.

As illustrated in FIGS. 71–73, the second terminal 162 includes the following: a platelike main body 162-1 of an electrically conductive, metallic member that is bent into a L-shape in cross-section; a contact portion 162-2 defined at one end portion of the main body 162-1, the contact portion 162-2 having a shape to contact the curved portion 160-5 of the first terminal 160; a cut and raised portion 162-3 formed substantially midway along the main body 162-1; a bent portion 162-4 formed by the other end portion of the main body 162-1 being slightly decreased in width dimension and further being bent into a L-shape in cross-section; and a swinging end portion 162-5 formed at an end portion of the bent portion 162-4, the swinging end portion 162-5 being bent toward the switch lever 140, i.e., in the downward direction of both FIG. 71B and FIG. 73B.

The platelike main body 162-1 of the second terminal 162 has resilient force imparted thereto. The main body 162-1 is thereby constructed to spring back to a predetermined L-shape in cross-section when no external forces are exerted on the main body 162-1.

The platelike main body 162-1 further has a dry cell-pressing portion 162-6 provided between the cut and raised portion 162-3 and the bent portion 162-4. The dry cell-pressing portion 162-6 is arcuate in shape, and protrudes toward the dry cell 128 so as to press and retain the dry cell 128 when the dry cell 128 is placed into the dry cell cap 108.

For example, a motor conforming to the specification of 1.5 volts and 7,000 rpm is preferably used as the motor 156. In this case, vibration frequency ranges from about 6,000 to about 8,000 cpm, e.g., some 7,000 cpm. Only for reference, in order to establish 7,000 rpm as the specification of the motor 156, determination is made in light of coil diameter, the number of windings, and voltage.

Figure 60:
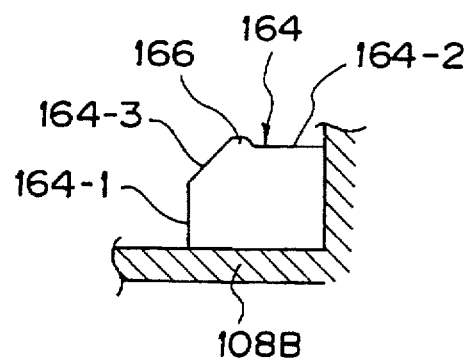
FIG. 60 is a schematic view showing a staged portion of the dry cell cap.
Figure 61:
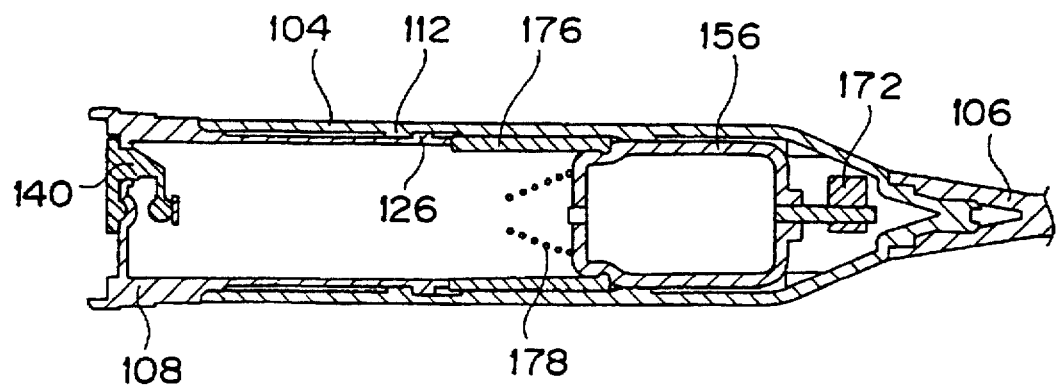
FIG. 61 is a schematic central enlarged transverse cross-sectional view showing the toothbrush.

As illustrated in FIG. 60, a scuff plate 164 is formed integrally with the inner surface of the discharging handgrip 124 when the dry cell cap 108 is formed from a resin material such as plastics. FIG. 60 shows that the scuff plate 164 includes the following: a wall surface portion 164-1 rising from the bottom 108B of the dry cell cap 108 toward the handle portion 104; a planar surface portion 164-2 extending parallel to the bottom 108B; and a slanted surface portion 164-3 having the wall surface portion 164-1 and the planar surface portion 164-2 in communication with one another. In addition, a convex portion 166, which protrudes toward the handle portion 104, is defined between the planar surface portion 164-2 and the slanted surface portion 164-3.

Reference numeral 168 denotes bristles, for example made of pig bristles or alternatively linear plastic members, either of which are disposed at one end 106a of the toothbrushing portion 106; 170 a revolving shaft of the motor 156; 172 an eccentric weight mounted eccentrically on the revolving shaft 170 for producing vibration as a result of the eccentric weight 172 being misaligned with the revolving shaft 170 when the eccentric weight 172 is driven by the motor 156; and 174 a projection formed on the inner surface of the dry cell cap 108 for retaining the dry cell 128.

Furthermore, for assembly of the toothbrush 102, a plastic spacer 176 is provided between the motor 156 and the dry cell cap 108.

Referring to FIGS. 80–86, the spacer 176 is shown including the following: a cylindrical main body 176-1; engagement arm portions 176-2 formed at one end of the main body 176-1 toward the motor 156 for engagement with the motor 156; and a guide groove portion 176-3 formed on the periphery of the main body 176-1 so as to serve as a guide for the electric circuit-connecting terminal 158 that intercommunicates the motor 156 and the dry cell 128.

Figure 82:
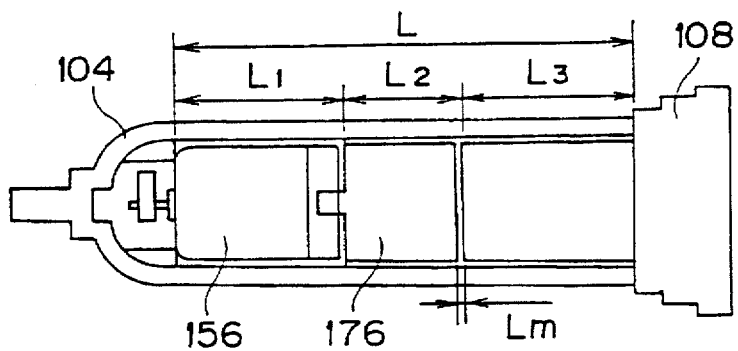
FIG. 82 is a schematic cross-sectional view of the toothbrush, illustrating a length relationship between the toothbrush, the handle portion, the motor, and the spacer.
Figures 83A, 83B:
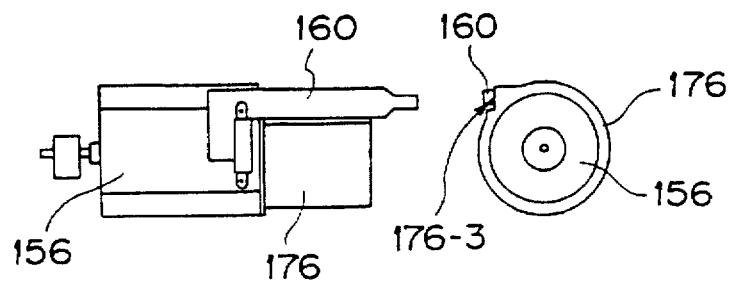
FIG. 83A is a plan view and FIG. 83B is a right side view.
Figure 84:
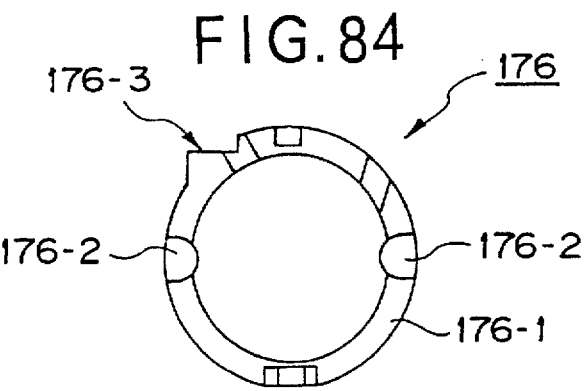
FIG. 84 is a plan view showing the spacer.
Figure 85:
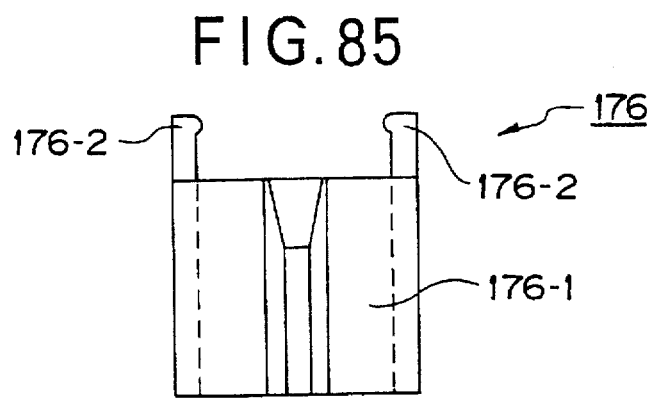
FIG. 85 is a front view showing the spacer.
Figure 86:
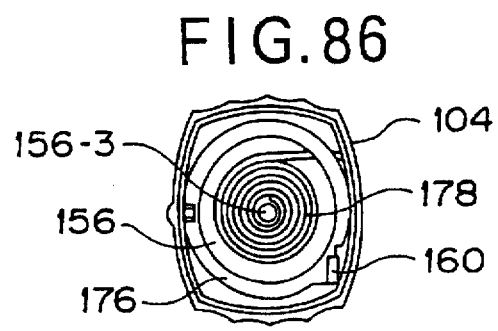
FIG. 86 is a bottom view showing the toothbrush when the motor is engaged with the spacer within the handle portion.
Figure 87:
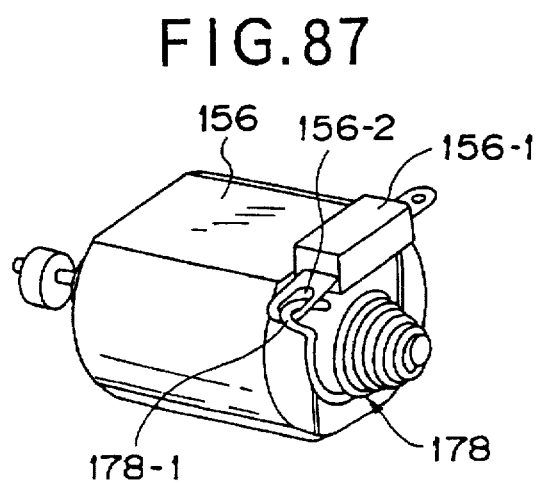
FIG. 87 is a schematic perspective view showing a coiled terminal in a state of being held against the motor.
Figure 88:
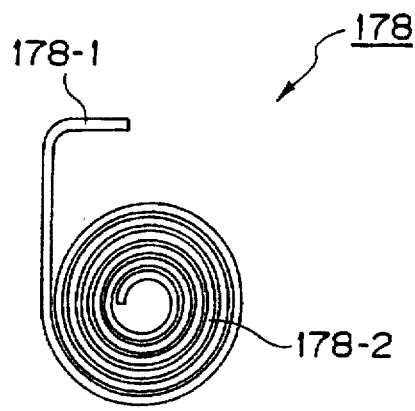
FIG. 88 is a front view showing the coiled terminal.
Figure 89:
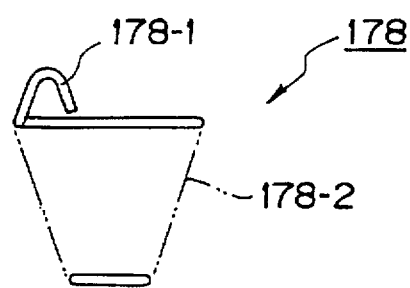
FIG. 89 is a plan view showing the coiled terminal.

As illustrated in FIG. 82, assuming that L is a distance between a predetermined position of the motor 156 and one end of the handle portion 104, then $L_1$ is an overall length of the motor 156; $L_2$ an overall length of the spacer 176; $L_3$ a length between one end of the dry cell cap 108 and the staged portion 136 of the dry cell cap 108; and Lm is a clearance between the spacer 176 and the dry cell cap 108, where $L=L_1+L_2+L_3+Lm$.

The electric circuit-connecting terminal 158 further has a coiled terminal 178 in addition to the aforesaid first and second terminals 160 and 162. The coiled terminal 178 is made of an electrically conductive, metallic member.

More specifically, the coiled terminal 178 includes a hook portion 178-1 and a taper-coiled portion 178-2, as illustrated in FIGS. 86–89. The hook portion 178-1 is a radially outward extending end portion of the coiled terminal 178, and is held in engagement with a hole 156-2 that is formed at a motor terminal 156-1 of the motor 156. The taper-coiled portion 178-2 is a resilient member looped around a motor cap convex portion 156-3 of the motor 156.

Figure 90:
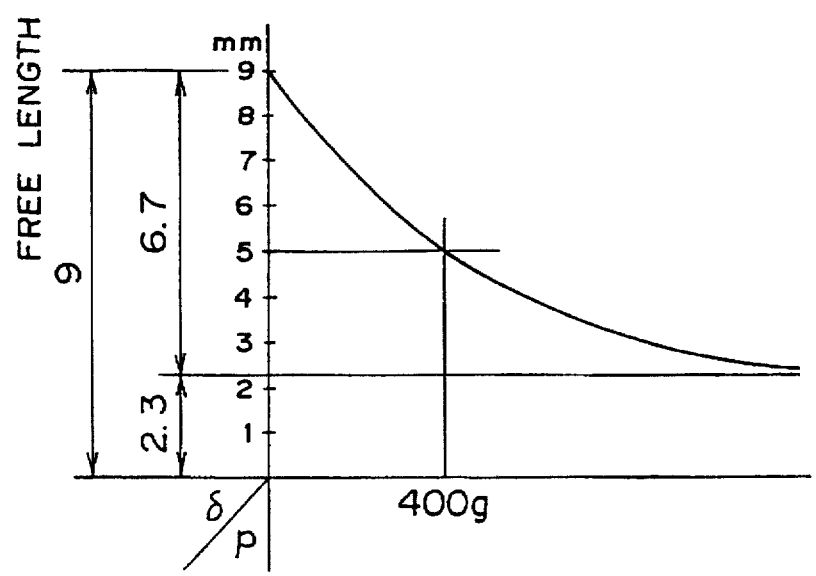
FIG. 90 is a view illustrating a free length of the coiled terminal.

As illustrated in FIG. 90, assuming that an entire free length of the coiled terminal 178 is 9 mm, then 2.3 mm is for the resilient member wound around the motor cap convex portion 156-3, while 6.7 mm is for the radially outward extending end portion.

Reference numeral 180 is a groove portion defined on the peripheral surface of the dry cell cap 108. Reference numeral 182 is an O-ring accommodated in the groove portion 180. The O-ring 182 is positioned between the handle portion 104 and the dry cell cap 108 when the cap 108 is fitted to the handle portion 104.

Next, the operation of the embodiment of FIGS. 49–90 will be described.

Figure 70A:
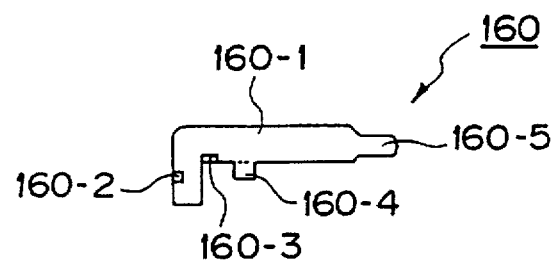
FIG. 70A is a plan view of the first terminal and FIG. 70B is a front view of the first terminal.
Figure 70B:
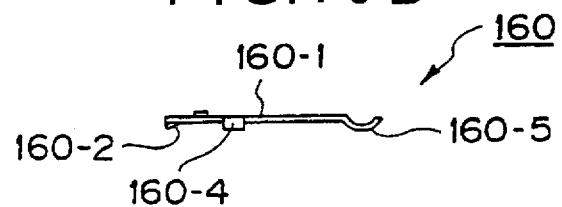

As illustrated in FIG. 70, when a dry cell cap 108 is detached from a handle portion 104 of the aforesaid electrically driven toothbrush 102, it is only necessary to produce the dry cell cap 108 out of the handle portion 104 through the aid of a staged portion 136 that is formed on the outer periphery of the dry cell cap 108, thereby releasing a state of engagement between first engagement protrusions 112 of the handle portion 104 and second engagement protrusions 126 of the dry cell cap 108.

Conversely, when an engagement surface portion 122 of the dry cell cap 108 is inserted into the handle portion 104, motor 156 and spacer 176 are initially placed within the handle portion 104. Then, the handle portion 104 and the dry cell cap 108 are arranged in alignment with one another using first and second protrusions 118 and 120 which lie on the respective outer peripheries of the handle portion 104 and dry cell cap 108. Next, the dry cell cap 108 is driven into the handle portion 104 while slit 132 of the dry cell cap 108 is brought into engagement with a positioning protrusion 116 of the handle portion 104.

When the first engagement protrusions 112 are engaged with the second engagement protrusions 126, a distal end portion of the engagement surface portion 122 is slightly reduced in dimension as a result of the dry cell cap 108 being defined with the slit 132. Consequently, easy engagement is achievable.

Figure 65:
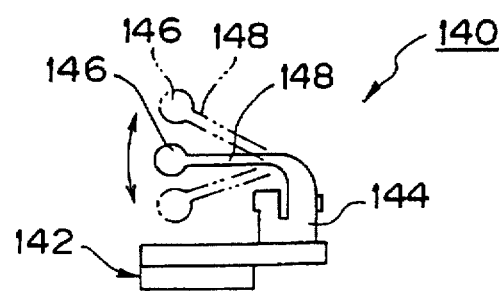
FIG. 65 is a schematic view showing the flexibility of an operating portion of the switch lever.

For assembly of the dry cell cap 108, the flexibility of the lever portion 148 of the switch lever 140 is utilized, as illustrated in FIG. 65. As shown in FIG. 66A through 66D, the operating portion 146 of the switch lever 140 is inserted into the dry cell cap 108 through the hole 138 of the dry cell cap 108. When the insertion is complete, the revolving shaft portion 144 of the switch lever 140 is fitted in the hole 138 in a watertight manner with the aid of the memory of the revolving shaft portion 144, as illustrated in FIG. 66E.

Figures 66A, 66B, 66C:
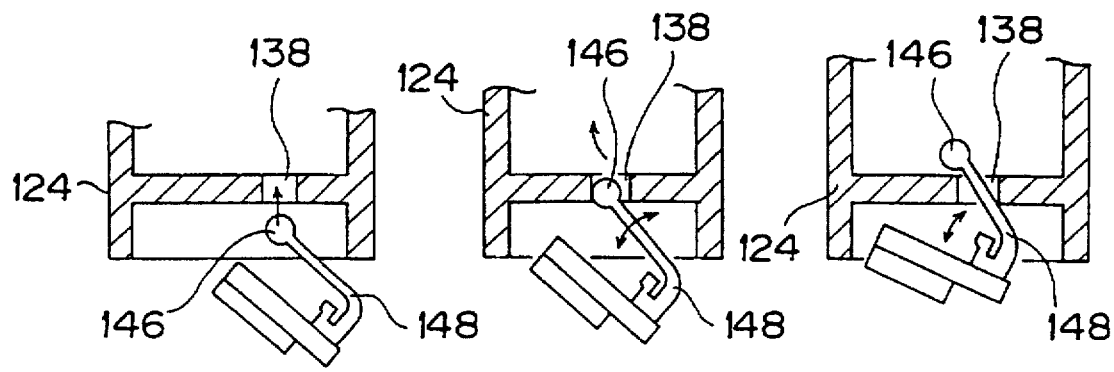
FIG. 66A is a schematic cross-sectional view showing an action before the operating portion of the switch lever is inserted into a hole of the dry cell cap.
FIG. 66B is a schematic cross-sectional view showing an action at the moment when the operating portion is inserted into the hole.
FIG. 66C is a schematic cross-sectional view showing an action after the operating portion is inserted through the hole.
Figures 66D, 66E:
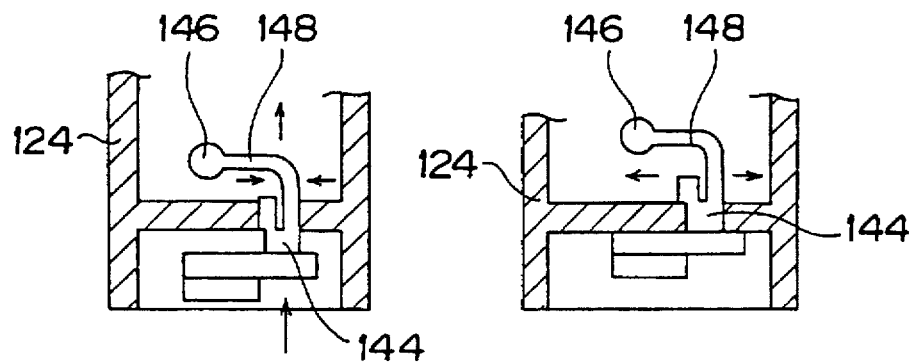
FIG. 66D is a schematic cross-sectional view showing an action at the moment when a revolving shaft portion of the switch lever is moved through the hole.
FIG. 66E is a schematic cross-sectional view showing the dry cell cap in a state of having the switch lever fitted thereto completely.

More specifically, as illustrated in FIG. 66D, the main shaft portion 144-1 and sub-shaft portion 144-2 of the revolving shaft portion 144 are directed to oppose one another in the hole 138 after the operating portion 146 is inserted through the hole 138. In addition, the slit 154 of the switch lever 140 brings the sub-shaft portion 144-2 closer in position to the main shaft portion 144-1 when these two shaft portions are moved through the hole 138. After the shaft portions 144-1 and 144-2 are driven through the hole portion 138, the sub-shaft portion 144-2 is spaced apart from the main shaft portion 144-1 by the returning force of the revolving shaft portion 144. As a result, the revolving shaft portion 144 is retained in a watertight manner.

As illustrated in FIGS. 74 and 75, for attachment of the electric circuit-connecting terminal 158, the first terminal 160 is initially attached to the motor 156 in engagement therewith through the utilization of the first cut and raised portion 160-2 at one end of the first terminal 160. Then, the contact portion 162-2, which is one end portion of the second terminal 162, is connected to the curved portion 160-5 which is the other end portion of the first terminal 160.

At this time, the curved portion 160-5 and the contact portion 162-2 are insecurely connected together in FIG. 76. However, it is possible to insure a positive connection between the curved portion 160-5 and the contact portion 162-2. That is, after the second terminal 162 is disposed on the inner surface of the dry cell cap 108, the cap 108 is inserted into the handle portion 104; and the curved portion 160-5 and the contact portion 162-2 are thereby brought into contact with one another.

Figure 78:
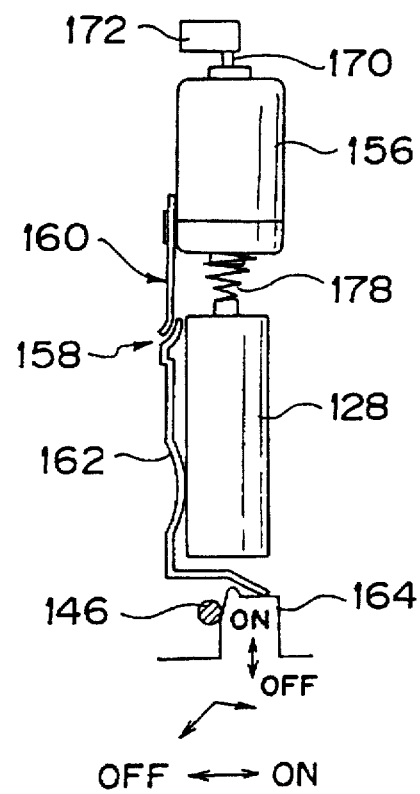
FIG. 78 is a schematic view illustrating an electric circuit-connecting terminal for use in the toothbrush.

As illustrated in FIG. 78, the second terminal 162 is positioned on the inner surface of the dry cell cap 108; and the bent portion 162-4 and the swinging end portion 162-5, both of which form the other end portion of the second terminal 162, are located adjacent to a negative terminal of the dry cell 128.

Figures 79A, 79B, 79C:
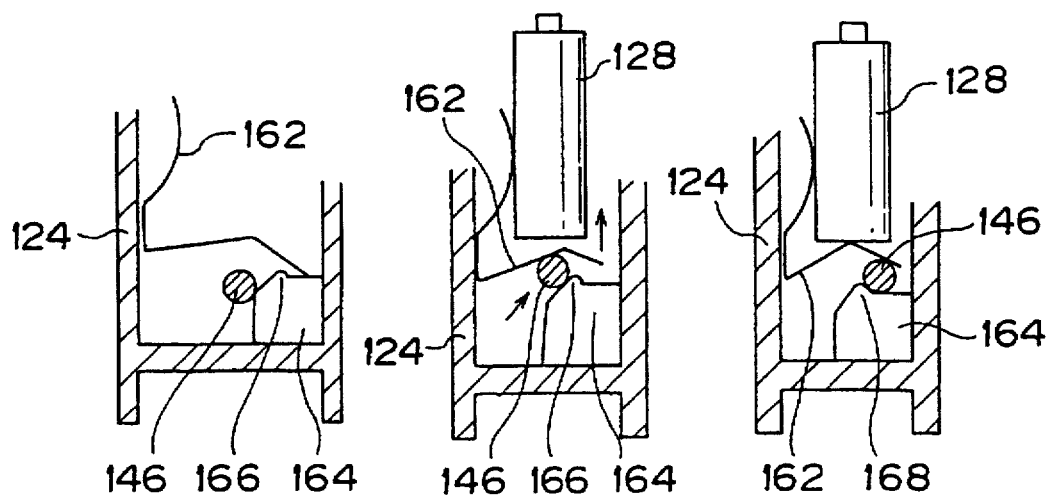
FIG. 79A is a schematic cross-sectional view, showing the operating portion of the switch lever when the switch lever is off.
FIG. 79B is a schematic cross-sectional view showing the aforesaid operating portion when the switch lever starts the on action.
FIG. 79C is a schematic cross-sectional view showing the aforesaid operating portion when the on action is complete.
Figure 80:
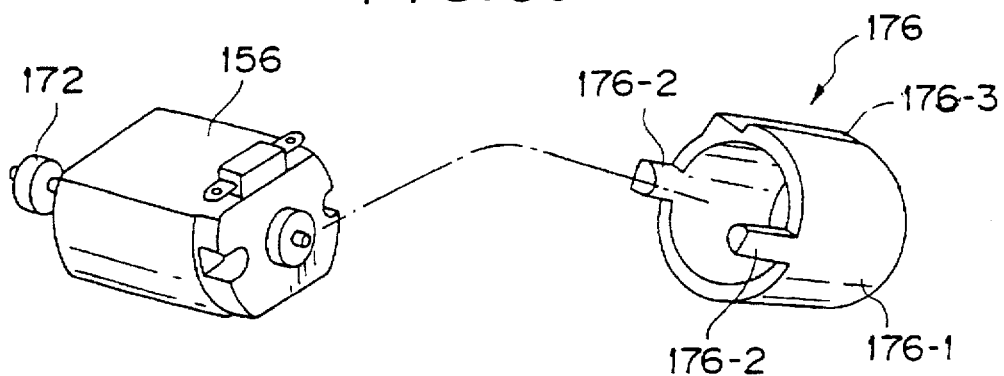
FIG. 80 is a schematic perspective view showing the motor and a spacer engaged with one another.
Figure 81:
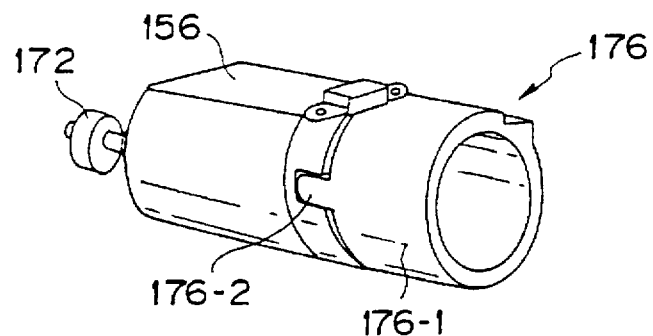
FIG. 81 is a schematic perspective view showing the motor and the spacer in a state of being held in engagement with one another.

When the manipulation control portion 142 of the switch lever 140 attached to the dry cell cap 108 is held and turned about the revolving shaft portion 144 of the switch lever 140 so as to provide and "on" action, the operating portion 146 of the switch lever 140 is caused to travel on the scuff plate 164, as illustrated in FIG. 79. That is, the operating portion 146 is first moved to the convex portion 166 through the wall surface portion 164-1 and the slanted surface portion 164-3. After riding on the convex portion 166, the operating portion 146 reaches the planar surface portion 164-2, thereby thrusting the swinging end portion 162-5 upward. As a result, the other end portion of the second terminal 162, or rather an intermediate portion between the bent portion 162-4 and the swinging end portion 162-5 is driven into contact with the negative terminal of the dry cell 128.

At this time, the dry cell-pressing portion 162-6 of the second terminal 162 presses the dry cell 128 with the aid of the resilient force of the dry cell-pressing portion 162-6. As a result, the dry cell 128 is reliably retained.

In a converse case of an "off" action, the manipulation control portion 142 is held and turned about the revolving shaft portion 144 in a reverse direction. Accordingly, the operating portion 146 is transferred from the planar surface portion 164-2 to the wall surface portion 164-1 through the convex portion 166 and the slanted surface portion 164-3, thereby releasing a state in which the operating portion 146 rides on the scuff plate 164. As a result, the intermediate portion of the second terminal 162 between the bent portion 162-4 and the swinging end portion 162-5 is lowered by urging forces, and is thus spaced apart from the negative terminal of the dry cell 128. In this way, the switch lever 140 provides an off action.

As a result, the band-shaped, first and second engagement protrusions 112 and 126 enables reliable engagement between the handle portion 104 and the dry cell cap 108. Accordingly, these two components 104 and 108 can be prevented from loosening after being engaged with one another. Further, it is possible to reduce wear and deformation at locations where the handle portion 104 and the dry cell cap 108 are engaged with one another.

In addition, the second terminal 162 is provided with the dry cell-pressing portion 162-6 which projects toward the dry cell 128; and when the dry cell 128 is placed into the dry cell cap 108, the dry cell-pressing portion 162-6 presses the dry cell 128 under the influence of the resilient force of the dry cell-pressing portion 162-6. As a result, the dry cell 128 can positively be retained, and thus can positively be prevented from emitting a rattling noise which would otherwise result from the vibration of the toothbrush 102 when the toothbrush 102 is used.

Furthermore, since the spacer 178 is positioned between the motor 156 and the dry cell cap 108 when the toothbrush 102 is assembled, the spacer 178 provides reliable positioning of the motor 156, and can prevent movement of the motor 156 within the handle portion 104.

Moreover, the electric circuit-connecting terminal 158 includes the first terminal member 160, the second terminal member 162, and the coiled terminal member 178. The coiled terminal 178 includes the hook portion 178-1 and the taper-coiled portion 178-2. The hook portion 178-1 is a radially outward extending end portion of the coiled terminal 178, and is held in engagement with the hole 156-2 that is formed at the motor terminal 156-1 of the motor 156. The taper-coiled portion 178-2 is a resilient member wound around the motor cap convex portion 156-3 of the motor 156. This construction facilitates mounting of the coiled terminal 178, and thus enables enhanced convenience of use.

Furthermore, for attaching the electric circuit-connecting terminal 158, the first terminal member 160 is attached to the motor 156 in engagement therewith with the aid of the first cut and raised portion 160-2 of the first terminal member 160; and the contact portion 162-2 of the second terminal member 162 is positioned on the curved portion 160-5 of the first terminal member 160, whereby the curved portion 160-5 and the contact portion 162-2 can be brought into contact with one another when the dry cell cap 108 is inserted into the handle portion 104. In addition, the hook portion 178-1 of the radially outward extending end portion of the coiled terminal member 178 is held in engagement with the hole 156-2 that is formed at the motor terminal 156-1 of the motor 156; and the taper-coiled portion 178-2 is wound around the motor cap convex portion 156-3 of the motor 156. This construction allows the electric circuit-connecting terminal 158 to be simplified in structure, which makes for easy fabrication at low cost.

Moreover, no urging means need be provided because the platelike main body 162-1 of the second terminal member 162 has resilient force imparted thereto so as to spring back to a predetermined L-shape in cross-section when no external forces are exerted on the platelike main body 162-1. As a result, a simple structure is achievable, and the electrically driven toothbrush 102 can be reduced in dimension.

Yet further, when a vibration frequency of the toothbrush 102 is established to be about 7,000 cpm, a high level of comfort can be obtained. Consequently, a feeling of discomfort is eliminated which would otherwise occur during toothbrushing.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an electrically driven toothbrush including a handle portion, an electrically operated motor accommodated in said handle portion, said motor having a shaft, a toothbrushing portion engaged with one end of said handle portion, a dry cell cap having a dry cell disposed therein so as to be engaged with the other end of said handle portion, said dry cell being selectively electrically connected to said motor, and an eccentric weight for producing vibration when said motor is actuated being mounted on said shaft of said motor, thereby bringing said toothbrushing portion into vibration which is utilized to clean the teeth, the improvement comprising: a switch lever received in a hole for switching said motor on and off, said hole being defined through an end wall of said dry cell cap, said switch lever includes a manipulation control portion positioned outside said dry cell cap when said switch lever is mounted on said dry cell cap, a revolving shaft portion fixedly attached to said manipulation control portion and sealingly but rotatably fitted in said hole, an operating portion positioned inside said dry cell cap, and a lever portion joined between said operating portion and said revolving shaft portion, said manipulation control, revolving shaft, operating, and lever portions of said switch lever are an integrally formed member, and said operating portion being ball-shaped and being joined to said lever portion.

2. A toothbrush according to claim 1, wherein said lever portion is L-shaped.

3. A toothbrush according to claim 1, wherein said switch lever is a flexible one-piece member.

4. A toothbrush according to claim 1, wherein said revolving shaft portion is joined at a second end of said lever portion.

5. A toothbrush according to claim 1, wherein said operating portion selectively completes an electrical circuit between said motor and said dry cell for actuating and deactuating said motor, and said lever portion is adapted to transmit a rotational motion of said revolving shaft portion to selectively position said operating portion.

6. In an electrically driven toothbrush including a handle portion, an electrically operated motor accommodated in said handle portion, said motor having a shaft, a toothbrushing portion engaged with one end of said handle portion, a dry cell cap having a dry cell disposed therein so as to be engaged with the other end of said handle portion, said dry cell being selectively electrically connected to said motor, and an eccentric weight for producing vibration when said motor is actuated being mounted on said shaft of said motor, thereby bringing said toothbrushing portion into vibration which is utilized to clean teeth, the improvement comprising: a switch lever received in a hole for switching said motor on and off, said hole being defined through an end wall of said dry cell cap, said switch lever includes a manipulation control portion positioned outside said dry cell cap when said switch lever is mounted on said dry cell cap, a revolving shaft portion fixedly attached to said manipulation control portion and sealingly but rotatably fitted in said hole, an operating portion positioned inside said dry cell cap, and a lever portion joined between said operating portion and said revolving shaft portion, said manipulation control, revolving shaft, operating, and lever portions of said switch lever are an integrally formed member, said handle portion has square corners therein, said dry cell cap has a handgrip part, and further including a positioning protrusion defined at each said corner of said handle portion at a predetermined distance from an end surface of said handle portion for fixing said dry cell cap in position, an engagement protrusion formed on an outer surface of said dry cell cap for engaging said positioning protrusions of said handle portion, and a stepped outer periphery defined on said handgrip part of said dry cell cap for permitting releasing engagement between said handle portion and said dry cell cap when said dry cell is to be replaced.

7. In an electrically driven toothbrush including a handle portion, an electrically operated motor accommodated in said handle portion, said motor having a shaft, a toothbrushing portion engaged with one end of said handle portion, a dry cell cap having a dry cell disposed therein so as to be engaged with the other end of said handle portion, and an eccentric weight for producing vibration when said motor is actuated being mounted on said shaft of said motor, thereby bringing said toothbrushing portion into vibration which is utilized to clean the teeth, the improvement comprising: a switch lever engaged with a hole for switching said motor on and off, said hole being defined through an end wall of said dry cell cap; and an electric circuit-connecting terminal means for joining said motor and said dry cell in communication with one another in order to actuate said motor, said electric circuit-connecting terminal means being formed by a first terminal member whose one end contacts said motor while the other end of said first terminal member extends toward said dry cell, and a second terminal member whose one end contacts the other end of said first terminal member while the other end of said second terminal member communicates with said switch lever and extends over said dry cell; said first terminal member including a platelike main body of an electrically conductive metallic member formed into a L-shaped configuration having shorter and longer legs, a first cut and raised tab portion formed on said shorter leg of said platelike main body, a second cut and raised tab portion formed on the longer leg of said platelike main body and adjacent to a location where the longer and shorter legs of said platelike main body are joined together, a bent portion formed adjacent to said second cut and raised tab portion, and a curved portion formed at an end portion of the longer leg of said platelike main body; said second terminal including a platelike primary body of an electrically conductive metallic member bent into a L-shaped configuration, a contact portion formed at one end portion of said platelike primary body for contacting said curved portion of said first terminal member, a cut and raised tab portion formed substantially midway along said platelike primary body, a bent portion formed by the other end portion of said platelike primary body being slightly decreased in width dimension and further being bent into a L-shape in cross-section, and a swinging end portion bent and formed at an end portion of said bent portion so as to be directed downward, and wherein said platelike primary body of said second terminal is resilient so as to return to a predetermined L-shaped configuration when no external forces are exerted on said platelike primary body of said second terminal.

8. A toothbrush according to claim 7, wherein said handle portion defines square corners therein, said dry cell cap has a handgrip part, and further including a positioning protrusion defined at each said square corner of said handle portion at a predetermined distance from an end surface of said handle portion for fixing said dry cell cap in position, an engagement protrusion formed on an outer surface of said dry cell cap for engaging said position protrusions of said handle portion, and a stepped outer periphery defined on said handgrip part of said dry cell cap for permitting releasing engagement between said handle portion and said dry cell cap when said dry cell is to be replaced.

9. A toothbrush according to claim 7, wherein said platelike primary body of said second terminal has a dry cell-pressing portion provided between said cut and raised tab portion and said bent portion, said dry cell-pressing portion being arcuate in shape and protruding toward said dry cell so as to press and retain said dry cell when said dry cell is placed into said cap.

10. An electrically driven toothbrush according to claim 9, wherein said motor has a motor terminal for receiving electricity to actuate said motor and a motor cap convex portion at an end of said motor, wherein said electric circuit-connecting terminal includes said first terminal, said second terminal, and a taper-shaped coiled terminal, and wherein said coiled terminal has one end portion held in engagement with a hole that is formed at said motor terminal of said motor, and said coiled terminal includes a resilient member looped around said motor cap convex portion of said motor.

* * * * *